US006350867B1

(12) United States Patent
Hart et al.

(10) Patent No.: US 6,350,867 B1
(45) Date of Patent: Feb. 26, 2002

(54) COMPOSITIONS AND METHODS FOR ENHANCING OSSEOUS GROWTH, REPAIR AND REGENERATION

(75) Inventors: Thomas C. Hart, Clemmons; Jennifer A. Price, Mooresville, both of NC (US)

(73) Assignee: Wake Forest University, Winston-Salem, NC (US)

( * ) Notice: Subject to any disclaimer, the term of this patent is extended or adjusted under 35 U.S.C. 154(b) by 0 days.

(21) Appl. No.: 09/031,962

(22) Filed: Feb. 27, 1998

(51) Int. Cl.[7] ........................ C07H 21/04; C07K 14/435
(52) U.S. Cl. .................... 536/23.5; 536/24.1; 536/24.3; 530/350
(58) Field of Search .............................. 536/23.5, 24.1, 536/24.3; 530/350

(56) References Cited

PUBLICATIONS

Alberts et al., Molecular Biology of the Cell, Jan. 1994, Garland Publishing, Inc., New York, NY.*
New England Biolabs 1995 catalog, p. 109, catalog #1014 and #1097.*
Meinkoth et al. Hybridization of nucleic acids immobilized on solid supports. Anal Biochem May 1984 1;138(2):267–284.*
Sambrook et al. Molecular Cloning: A Laboratory Manual Second Edition vols. 1, 2 and 3. Cold Spring Harbor Laboratory Press: Cold Spring Harbor, New York, U.S.A. Nov., 1989, p. 11.47.*
Cross et al. Purification of CpG islands using a methylated DNA binding column. Nat Genet. Mar. 1994;6(3):236–44, May 1984.*
Price, J.A., D.W. Bowden, J.T. Wright, M.J. Pettenati, and T.C. Hart. Identification of a Mutation in DLX3 Associated With Tricho–Dento–Osseous (TDO) Syndrome. *Human Molecular Genetics*. 1998. 7:563–569.
Hart, T.C., D.W. Bowden, J. Bolyard, K. Kula, K. Hall, and J.T. Wright. Genetic Linkage of the Tricho–Dento–Osseous Syndrome to Chromosome 17q21. *Human Molecular Genetics*. 1997. 6:2279–2284.
McGuinness, T., M.H. Porteus, S. Smiga, A. Bulfone, C. Kingsley, M. Qiu, J.K. Liu, J.E. Long, D. Xu, and J.L.R. Rubenstein. Sequence, Organization, and Transcription of the DLx–1 and DLx–2 Locus. *Genomics*. 1996. 35:473–485.
Weiss, K.M., F.H. Ruddle, and J. Bollekens. Dlx and Other Homeobox Genes in the Morphological Development of the Dentition. *Connective Tissue Research*. 1995. 32:35–40.
Sharpe, P.T. Homeobox Genes and Orofacial Development. *Connective Tissue Research*. 1995. 32:17–25.
Wright, J.T., M.W. Roberts, A.R. Wilson, and R. Kudhail. Tricho–Dento–Osseous Syndrome. *Oral Surgery Oral Medicine Oral Pathology*. 1994. 77:487–493.

Maas, R., and M. Bei. The Genetic Control of Early Tooth Development. *Crit Rev Oral Biol Med*. 1997. 8:4–39.
Kula, K., K. Hall, T. Hart, and J.T. Wright. Craniofacial Morphology of the Tricho–Denot–Osseous Syndrome. *Clinical Genetics*. 1996. 50:446–454.
Wright, J.T., K. Kula, K. Hall, J.H. Simmons, and T.C. Hart. Analysis of the Tricho–Dento–Osseous Syndrome Genotype and Phenotype. *American Journal of Medical Genetics*. 1997. 72:197–204.
Weiss, K.M., J. Bollekens, F.H. Ruddle, and K. Takashita. Distal–Less and Other Homeobox Genes in the Development of the Dentition. *The Journal of Experimental Zoology*. 1994. 270:273–284.
Nakamura, S., D.W. Stock, K.L. Wydner, J.A. Bollekens, K. Takeshita, B.M. Nagai, S. Chiba, T. Kitamura, T.M. Freeland, Z. Zhao, J. Minowada, J.B. Lawrence, K.M. Weiss, and F.H. Ruddle. Genomic Analysis of a New Mammalian Distal–Less Gene: DLx7. *Genomics*. 1996. 38:314–324.
Papalopulu, N., and C. Kintner. Xenopus Distal–Less Related Homeobox Genes are Expressed in the Developing Forebrain and are Induced by Planar Signals. *Development*. 1993. 117:961–975.
Dirksen, M.L., M.I. Morasso, T.D. Sargent, M. Jamrich. Differential Expression of a Distal–Less Homeobox Gene XdLL–2 in Ectodermal Cell Lineages. *Mechanisms of Development*. 1994. 46:63–70.
Simeone, A., D. Acampora, M. Pannese, M. D'Esposito, A. Stornaiuolo, M. Gulisano, A. Mallamaci, K. Kastury, T. Druck, K. Huebner, and E. Boncinelli. Cloning and Characterization of Two Members of the Vertebrate DLx Gene Family. *Proc. Natl. Acad. Sci. USA*. 1994. 91:2250–2254.
Thomas, B.L., M.H. Porteus, J.L.R. Rubenstein, and P.T. Sharpe. The Spatial Localization of DLx–2 During Tooth Development. *Connective Tissue Research*. 1995. 32:27–34.
Robinson, G.W., and K.A. Mahon. Differential and Overlapping Expression Domains of Dlx–2 and Dlx–3 Suggest Distinct Roles for Distal–Less Homeobox Genes in Craniofacial Development. *Mechanisms of Development*. 1994. 48:199–215.

(List continued on next page.)

Primary Examiner—David S. Romeo
(74) Attorney, Agent, or Firm—Dann, Dorfman, Herrell and Skillman

(57) ABSTRACT

Novel human DLX3 genes and their encoded proteins are provided herein. The proteins encoded by the disclosed DLX3 and DLX3Δ genes play a pivotal role in craniofacial growth and development. DLX3 genes and their encoded proteins provide valuable therapeutic targets for the design of proliferative agents which augment bone growth and repair.

10 Claims, 7 Drawing Sheets

OTHER PUBLICATIONS

Akimenko, M.A., M. Ekker, J. Wegner, W. Lin, and M. Westerfield. Combinatorial Expression of Three Zebrafish Genes Related to Distal–Less: Part of a Homeobox Gene Code for the Head. *The Journal of Neuroscience*. 1994. 14:3475–3486.

Jowett, A.K., S. Vainio, M.W.J. Ferguson, P.T. Sharpe, and I. Thesleff. Epithelial–Mesenchymal Interactions are Required for msx 1 and msx2 Gene Expression in the Developing Murine Molar Tooth. *Development*. 1993. 117:461–470.

Qiu, M., A. Bulfone, I. Ghattas, J.J. Meneses, L. Christensen, P.T. Sharpe, R. Presley, R.A. Pedersen, and J.L.R. Rubenstein. Role of the Dlx Homeobox Genes in Proximodistal Patterning of the Branchial Arches: Mutations of Dlx–1, Dlx–2, and Dlx–1 and –2 Alter Morphogenesis of Proximal Skeletal and Soft Tissue Structures Derived from the First and Second Arches. *Developmental Biology*. 1997. 185:165–184.

* cited by examiner

Exon 1
DLX3E1F ⟶

```
 -67  tcttgcactccggtccgttcctgtcctctgcggaggccagccctggggaggtgcagcgcc   -8
  -7  cgccaggATGAGTGGCTCCTTCGATCGCAAGCTCAGCAGCATCCTCACCGACATCTCCAG    53
   1          M  S  G  S  F  D  R  K  L  S  S  I  L  T  D  I  S  S   18
  54  CTCCCTTAGCTGCCATGCGGGCTCCAAGGACTCGCCTACCCTGCCCGAGTCTTCTGTCAC   113
  19   S  L  S  C  H  A  G  S  K  D  S  P  T  L  P  E  S  S  V  T    38
 114  TGACCTGGGCTACTACAGCGCTCCCCAGCACGATTACTACTCGGGCCAGCCCTATGGCCA   173
  39   D  L  G  Y  Y  S  A  P  Q  H  D  Y  Y  S  G  Q  P  Y  G  Q    58
 174  GACGGTGAACCCCTACACCTACCACCACCAATTCAATCTCAATGGGCTTGCAGGCACGGG   233
  59   T  V  N  P  Y  T  Y  H  H  Q  F  N  L  N  G  L  A  G  T  G    78
 234  CGCTTACTCGCCCAAGTCGGAATATACCTACGGAGCCTCCTACCGGCAATACGGGGCGTA   293
  79   A  Y  S  P  K  S  E  Y  T  Y  G  A  S  Y  R  Q  Y  G  A  Y    98
 294  TCGGGAGCAGCCGCTGCCAGCCCAGGACCCAGgtgagggccacggggtcgcgaggacagt   353
  99   R  E  Q  P  L  P  A  Q  D  P  V                              108
 354  gggagacactggaa                                                 367
         ⟵DLX3E1R
```

Exon 2
DLX3E2F ⟶

```
1310  gagtcggtgggcggaagcgaggggcgtccggcggggccctggagggtcgcaggagtcgca  1369
1370  ggccgaggctgaaccgcccctcttccgcccggtgcgttccccgcagTGTCGGTGAAGGAG  1429
 109                                                  S  V  K  E   113
1430  GAGCCGGAAGCAGAGGTGCGCATGGTGAATGGGAAGCCCAAGAAGGTCCGAAAGCCGCGT  1489
 114   E  P  E  A  E  V  R  M  V  N  G  K  P  K  K  V  R  K  P  R   133
1490  ACAATCTACTCCAGCTACCAGCTGGCCGCCCTGCAGCGCCGCTTCCAGAAGGCCCAGTAC  1549
 134   T  I  Y  S  S  Y  Q  L  A  A  L  Q  R  R  F  Q  K  A  Q  Y   153
1550  CTGGCGCTGCCCGAGCGCGCCGAGCTGGCCGCGCAGCTGGGCCTCACGCAGACACAGgtt  1609
 154   L  A  L  P  E  R  A  E  L  A  A  Q  L  G  L  T  Q  T  Q      172
1610  ggtgtttggctgtccagggtcgcgggggcgcgcgggaccccgtagttccccgcgcgctgc  1669
1670  cgagtctggctggccactgaagggccctgcgggctcctggaactcttgcctttggg      1725
                                              ⟵DLX3E2R
```

Exon 3
DLX3E3F ⟶

```
2973  aggccacaattctatcccagatccaagaaaactgggagtcaggaagcctgttttttgcctg  3032
3033  attcttatgtgaaattggggttctggcctttcttttttcttggctaggttcttgccagggtt  3092
3093  gttttagcat[tctgagaggctaactag]ctaccctttcttctctggcccagGTGAAAATC  3152
 173              DLX3mut1                             del V  K  I   175
                                                       ttt
3153  TGGTTCCAGAACCGCCGTTCCAAGTTCAAGAAACTCTACAAGAACGGGGAGGTGCCGCTG  3212
 176   W  F  Q  N  R  R  S  K  F  K  K  L  Y  K  N  G  E  V  P  L   195
3213  GAGCACAGTCCCAATAA[CAGTGATTCCATGGCCTGC]AACTCACCACCATCACCCGCCCTC  3272
 196   E  H  S  P  N  N  S  D  S  M  A  C  N  S  P  P  S  P  A  L   215
3273  TGGGACACCTCTTCCCACTCCACTCCGGCCCCTGCCCGCAGTCAGCTGCCCCCGCCGCTC  3332
 216   W  D  T  S  S  H  S  T  P  A  P  A  R  S  Q  L  P  P  P  L   235
3333  CCATACAGTGCCTCCCCCAGCTACCTGGACGACCCCACCAACTCCTGGTATCACGCACAG  3392
 236   P  Y  S  A  S  P  S  Y  L  D  D  P  T  N  S  W  Y  H  A  Q   255
3393  AACCTGAGTGGACCCCACTTACAGCAGCAGCCGCCTCAGCCAGCCACCCTGCACCATGCC  3452
 256   N  L  S  G  P  H  L  Q  Q  Q  P  P  Q  P  A  T  L  H  H  A   275
3453  TCTCCCGGGCCCCCGCCCAACCCTGGGGCTGTGTACTGAgcaccatctggcctgcaccct  3512
 276   S  P  G  P  P  P  N  P  G  A  V  Y  *                       288
3513  tgacaaaggacccaggaccaggc                                        3536
```

Figure 2

```
Human DLX3     SVKEEPEAEV RMVNGKPKKV RKPRTIYSSY QLAALQRRFQ KAQYLALPER
Mouse dlx3     ---------- ---------- ---------- ---------- ----------
Axolotl dlx3   ------P--- ---------- ---------- ---------- ----------
Newt NvHBox-4  T-----P--- ---------- -------I-- ---------- ----------
Zebrafish dlx3 A-----T--- ---------- -------I-- ---------- ----------
Xenopus X-dll2 ------T--- ---------- -------I-- ---------- ----------
Human DLX2     E.--DL-P-I -I-------- ---------- -------F-- -------T--
Human DLX5     ---------- ---------- ---------- -------F-- -------T--
Human DLX1     ---------- ---------- I--------- ---Q--NR-- -------QT-
Human DLX6     ---------- ---------- I--------- ---Q--NH-- -------QT-
Human DLX7     P.RLS--PSE -RPQAAA--L ---------- ---QH-NQ-- -------HT- ↓
Human DLX3     AELAAQLGLT QTQVKIWFQN RRSKFKKLYK NGEVP.LEHSP NNSDSMACNS
Mouse.dlx3     ---------- ---------- ---------- ----------- ----------
Axolotl dlx3   ---------- ---------- ---------- -----.--GM- --D-------
Newt NvHBox-4  ---------- ---------- ---------- -----.--GM- ----------
Zebrafish dlx3 ---------- ---------- ---------- -----.---.- --A-------
Xenopus X-dll2 ---------- ---------- ---------- ---G-DM---- -------G--
Human DLX2     ---------- ---------- ----MW---- S--I-SEQ-PG ASASPPCASP
Human DLX5     -----S---- ---------- K---I--IM- ---N------- ----------
Human DLX1     -----S---- ---------- K--------M- Q-GAA------ ----------
Human DLX6     -----S---- ---------- K--------L- Q-SN------- ----------
Human DLX7     -Q-------- ---------- K---Y-----L- QNSGGQEGD.F PGRTFSVSPC
```

FIGURE 3 normal deleted

Family 1
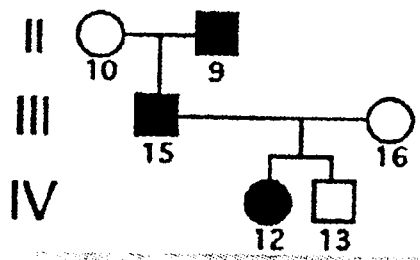
Family 2
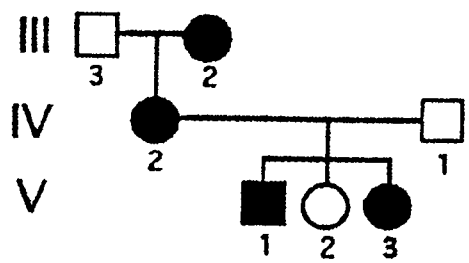
FIG. 5

```
   1  GTGACGCGCG  TAATACAATC  ACTATAGGGC  GAATTGGGTA  CCGGGCCCCC
  51  CCTCGAGGTC  GACGGTATCG  ATAAGCTTGA  TATCGAATTC  CTGCAGAGCT
 101  CGAAGGAACC  ACGAGGTGGC  GCGCTAGCAC  TGCGTTCGCC  CGGCGAGGCA
 151  NGGCGAGTGG  ACGTGGGGTC  NACGGAGCGA  GCCGGGCAGG  CTGGGAACTG
 201  ANATTTGGAT  TCTCTCCCCC  AAANAAAGGC  GAAGGGCNAA  ATGGGGTGTG
 251  GGAGGCAGGG  ATNAGCTANA  CGTTGGGAAC  AGCTANCATG  ACCTANGGGG
 301  CCCAGCTTGG  TGGGCTAGAC  NGGACTAAAA  TCTGGGGGTC  CCCACAGAGG
 351  GGANCCATTC  TTCANGGMTY  YYCYGGTGCT  RCGAGGANTT  CAGTGGAGCN
 401  GTACANCTCC  CNSCTACTGG  AGATGARGAA  NGTNCTAAGC  GGTCTANACA
 451  CWTCTGCCTA  CAACCACATG  TTCACACGCG  GATGGCCCTC  CACTCATNCT
 501  GCCTGCACCC  CGCCCCCGAC  ACACTCCTGC  MTGCATGTAC  CTCTGTTGGA

551  TWCTGTGGAA  CACATNAAAN  TCCTCACATC  ACNCACCCCA  AATAYANTTC
 601  KTCCCATGCA  NCCAGTCCCC  AANAAGTNTC  CCAATTCCNC  ANTGCTGTCC
 651  CNTNATACCM  CAAAATCTGC  CCTTCARANT  TACTNNNAAK  CACACAGTCA
 701  CAGANCCAGC  CTGTGTCCAC  CCAACCTCGT  GGGGACCCAA  GTCCTTGCTA
 751  CCTTCAGCAA  GAATGGGGNC  ATCTGTGAAA  CTGCACATAC  ATANCTTTGG
 801  GAGATAATTC  TGGTATCACC  GGACAGGCTG  TACATCCCCA  ACAACCTCTA
 851  AATCCACACA  GGTCTGCTTC  CCCTTCTCCA  ATAGGATCCT  CCTAGTGCTA
 901  AATTATGTCT  TTCATAGGCT  CAAGAACATT  NCTT~GCCCG  GTGGGCACCT
 951  TCCTAAATAA  AAAGAAAATT  TTTTAAATTA  CGTTTTTGTA  ATTATGTAAT
1001  ACAAGGATAT  AATAGCAATG  ACTGCATTGC  TATTAAGATA  ATATATTAAT
1051  ATCATATATT  CAAACATTCT  CTTTCACCTA  AAAGGTGTTT  TCCTTTTCTT
1101  CTGATTTTAA  GANAAACCAT  TTTCAGGGGC  TGTGAGTCCT  CACCACTTTG
1151  GGTACATTTG  TGTGCCTGTC  ATTTGCACAG  TGCGTGCACA  CGTGTGCACA
1201  CACACACAAC  CATACCCCAC  CTTAGACCAT  CTCTTTCCAC  AAACACACAA
1251  TGGGCAAACT  CCCCTCCTTG  CCCACCTCAC  CTAAGCCCAT  CTCTCATCCC
1301  CCAGCCAGAG  AAACAGACTG  ACAGATCCTG  GGGGCTCCAC  AGANCAACCC
```

Figure 6

```
1351   TTCCCCTCCA  CCTCCACGCC  CCTCCTTCAG  AAAACTTATC  TGGGCTGGAG
1401   CTACAAGAAW  WAMSRRGGGT  GTGTGTGTGT  GTGTGTGTGT  GTGTGTGTGT
1451   GTGTGTGTGT  GTGTTTTGAG  TAACAACAAA  GACTGGGGAA  AAAGAAGAGA
1501   GAGGAGGGAG  GAGAGAAGGA  AAAGGGGGAG  AGAGAGAGAG  AGAGAGGAGA
1551   GCATAGGAGC  GAGAGAGCAA  AAGCGTGTTT  TGCCTGGAAG  GCAAGACTTG
1601   CAGCCAATCA  GCGCGTANGA  GCCTCCCTCG  GCGACTCCAC  TATTGAGTCT
1651   ATAACCGGCT  GGCCGGGCGG  AGCTGGCANC  ATTTGATTGT  GGCTTGGGAC
1701   GCGAGGAGAG  GCGCGCAGCG  ACCGCCTGAC  GGCAGGCAAT  GGTGTNNGCG
1751   CCTCTCGGCC  TCCCCCTCCC  CCCAGACGCG  GCCGGGTCCT  CCCTTCGCCT
1801   TCTGGACACA  CACCCCTGCC  TCGTCTCTTC  CGCCTCTCTT  GCACTCCGGT
1851   CCGTTCCTGT  CCTCTGCGGA  GGCCAGCCCT  GGGGAGGTGC  AGCGCCCGCC
1901   AGGATG
```

COMPOSITIONS AND METHODS FOR ENHANCING OSSEOUS GROWTH, REPAIR AND REGENERATION

Pursuant to 35 U.S.C. §202(c) it is acknowledged that the U.S. Government has certain rights in the invention described herein, which was made in part with funds from the National Institutes of Health, grant number, R29/DE10990.

FIELD OF THE INVENTION

This invention relates to the fields of molecular biology and bone physiology. More specifically, the invention provides novel compositions and methods for enhancing osseous growth, repair and regeneration.

BACKGROUND OF THE INVENTION

Several publications are referenced in this application by numerals in parentheses in order to more fully describe the state of the art to which this invention pertains. The disclosure of each of these publications is incorporated by reference herein.

Bone growth and development is a complex process involving the participation of many genes and proteins. The normal development of hair, teeth and bone involves extensive epithelial-mesenchyme interactions. For example, the tooth develops through interactions between oral ectoderm of epithelial origin which eventually produces enamel, while mesenchyme cells from the neural crest produce dentin and supportive structures (10).

Studies in vertebrate organisms have implicated the involvement of a number of genes in craniofacial development, including transcription factor and growth factor genes (10). Several homeobox genes are also known to be expressed in the developing teeth. These genes are postulated to function together with growth factors, such as bone morphogenic proteins and members of the transforming growth factor-beta genes, in the complex developmental pathways involved in craniofacial growth and development.

SUMMARY OF THE INVENTION

The present invention relates to the identification of novel nucleic acid molecules and proteins encoded by such nucleic acid molecules or degenerate variants thereof, that participate in the control of mammalian bone growth, development and regeneration.

Provided herein are novel compositions and methods for enhancing osseous growth, repair and regeneration. According to one aspect of the invention, an isolated nucleic acid molecule is provided which includes a complete coding region for a homeobox domain-containing DLX3 protein of a predicted size between about 25 and 35 kilodaltons.

In a preferred embodiment of the invention, an isolated nucleic acid molecule is provided that includes a cDNA encoding a human DLX3 protein. In a particularly preferred embodiment, the human DLX3 protein has an amino acid sequence the same as Sequence I.D. No. 2. An exemplary DLX3 encoding nucleic acid molecule of the invention comprises Sequence I.D. No. 1.

According to another aspect of the invention, another isolated nucleic acid molecule is provided which includes a complete coding region for a DLX3Δ protein also containing a homeobox domain of a size between about 20 and 35 kilodaltons. DLX3Δ appears to be a mutated form of DLX3 associated with Tricho-Dento-Osseous (TDO) syndrome. The rare genetic polymorphism present in DLX3Δ is correlated with the expression of a DLX3Δ protein, which is associated with increased bone thickness and density.

In a preferred embodiment of the invention, an isolated nucleic acid molecule is provided that includes a cDNA encoding a human DLX3Δ protein. In a particularly preferred embodiment, the human DLX3Δ protein has an amino acid sequence the same as Sequence I.D. No. 4. An exemplary dlx3Δ nucleic acid molecule of the invention comprises Sequence I.D. No. 3.

According to another aspect of the present invention, an isolated nucleic acid molecule is provided, which has a sequence selected from the group consisting of: (1) Sequence I.D. No. 1; (2) a sequence specifically hybridizing with preselected portions or all of the complementary strand of Sequence I.D. No. 1; (3) a sequence encoding preselected portions of Sequence I.D. No. 1, (4) a sequence encoding part or all of a polypeptide having amino acid Sequence I.D. No. 2; (5) Sequence I.D. No. 3; (6) a sequence specifically hybridizing with preselected portions or all of the complementary strand of Sequence I.D. No. 3; (7) a sequence encoding preselected portions of Sequence I.D. No. 3, and (8) a sequence encoding part or all of a polypeptide having amino acid Sequence I.D. No. 4. Such partial sequences are useful as probes to identify and isolate homologues of the DLX3 genes of the invention. Accordingly, isolated nucleic acid sequences encoding natural allelic variants of the nucleic acids of Sequence I.D. Nos., 1, or 3 are also contemplated to be within the scope of the present invention. The term "natural allelic variants" will be defined hereinbelow.

In another aspect of the invention, a nucleic acid molecule comprising the upstream 5' untranslated region of the DLX3 gene is provided herein as Sequence I.D. NO: 5. This sequence provides regulatory elements that control the expression of the DLX3 proteins of the invention. Accordingly, the sequence may be genetically manipulated using recombinant DNA tecniques known to those of skill in the art to enhance or inhibit the expression of DLX3 proteins.

According to another aspect of the invention, antibodies immunologically specific for the proteins described hereinabove are provided.

In addition, this invention presents methods for genetic screening and diagnostic evaluation of patients at risk for TDO. Additionally, the nucleic acids of the invention may be used for prenatal genetic screening. The hybridization specificity of the nucleic acids of the invention may be also be used for differential evaluation of patients presenting with phenotypic characteristics commmon to TDO, such as amelogenesis imperfecta. For example, nucleic acid molecules of the invention can be used as diagnostic hybridization probes or as primers for diagnostic PCR analysis for the identification of DLX3 mutations. Additionally, human DLX3 genomic sequences are provided which can be used to selectively amplify human DLX3 exons for analysis.

Further, methods and compositions are provided for enhancing growth, development and repair of osseous structures. Addition of DLX3Δ proteins and DLX3Δ-encoding nucleic acids should serve to enhance bone thickness and increase bone density at the sites of application. Exogenously added DLX3Δ proteins and DLX3Δ-encoding nucleic acids should have utility in the treatment of bone/osseous defects secondary to trauma, such as broken bones. Finally, the DLX3Δ proteins and nucleic acids of the invention should also have utility in the treatment of defects secondary to certain pathologies, such as periodontal disease defects or congenital/acquired defects such as osteoporosis.

BRIEF DESCRIPTION OF THE DRAWINGS

FIG. 2 shows the nucleotide sequence (SEQ ID NO:14) and predicted amino acid sequence (SEQ ID NO:2) of the human DLX3 gene. Nucleotides are numbered based on genomic sequence information with number 1 representing the first nucleotide of the first codon. The protein sequence is numbered sequentially from the initiation codon. Uppercase letters in the nucleotide sequence indicate protein coding regions, lowercase letters represent intronic or untranslated regions. The homeobox is shown by a double underline. Primer sequences used in PCR amplification and sequencing of affected and unaffected TDO family members are underlined. Primers (DLX3mut1 and DLX3mut2) used in the mutation analysis are boxed. The four base pair deletion found in one allele of all affected TDO members is shown at position 3198–3201.

FIG. 3 shows the protein alignments of the homeodomain region of dlx family members. The homeobox region is boxed. Hyphens (-) indicate conserved residues, spaces indicate unavailable protein sequences. The arrow indicates the first amino acid affected by the frameshift mutation in TDO patients. Organisms and Genbank accession numbers are as follows: human DLX3 (AF028233residues 110 to 209 of SEQ ID NO: 2), mouse dlx3 (Q64205; SEQ ID NO: 15), zebrafish dlx3 (S23279; SEQ ID NO: 18), Xenopus dlx3 (HMD2_XENLA; SEQ ID NO: 19), axolotl dlx3 (Q90229; SEQ ID NO: 16), newt dlx3 (BOX4_NOTVI; SEQ ID NO: 17), human DLX2 (Pn0670; SEQ ID NO: 20), human DLX5 (C53495; SEQ ID NO: 21), human DLX1 (A53495; SEQ ID NO: 22), human DLX6 (D53495; SEQ ID NO: 23), and human DLX7 (Q92988; SEQ ID NO: 24).

FIG. 5 shows the pedigrees and PCR deletion analysis of portions of two TDO families. Pedigree numbers correlate to those previously described (29). All affected TDO individuals exhibit the normal 145 bp allele and the 141 bp deleted allele. Unaffected individuals only exhibit the normal 145 bp allele.

FIG. 6 shows the 5' untranslated region of DLX3 (SEQ. ID NO: 5).

DETAILED DESCRIPTION OF THE INVENTION

Figure 1:
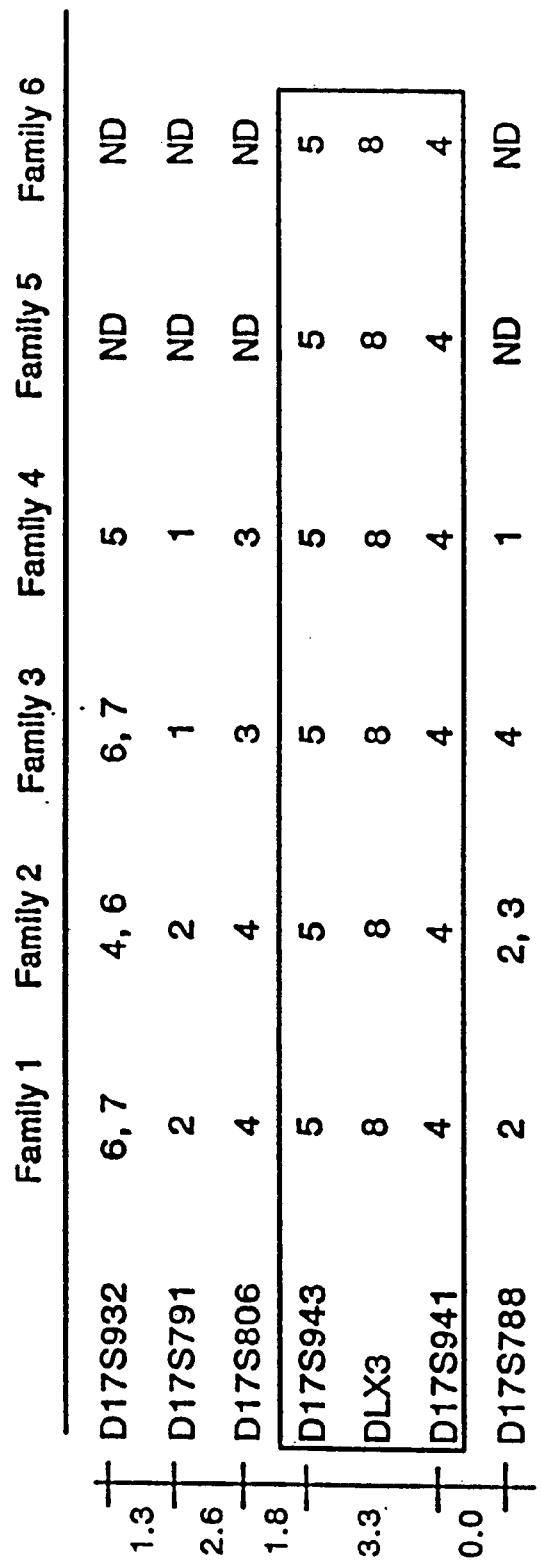
FIG. 1 is a table showing the results of haplotype analysis of TDO families illustrating the alleles which segregate with the TDO phenotype. ND indicates the genotypes were not determined. No recombination is observed between D17S91 and D17S41 and the TDO gene in any of the families. Genetic distances in centiMorgans between the polymorphic markers are depicted at the left of the table. The common haplotype region is boxed.

Tricho-Dento-Osseous syndrome (TDO) is an autosomal dominant disorder characterized by abnormal hair, teeth, and bone. The main clinical manifestations of TDO include taurodontism, enamel hypoplasia, kinky, curly hair at birth, and increased thickness and density of the cranial bones. These pleiotropic clinical features suggest the role of a developmental gene modulating epithelial-mesenchymal interactions. The TDO locus was recently mapped to chromosome 17q21, a region that includes two members of the distal-less homeobox gene family, DLX3 and DLX7 (28, 29). The genomic cloning and sequencing of both human DLX3 and DLX7 is described herein. The identification of a four base deletion in human DLX3 which correlates with the TDO phenotype in six families is also described. The observed mutation is predicted to cause a frameshift and premature termination codon, resulting in a functionally altered DLX3.

To identify genes that are involved in craniofacial development TDO (Mendalian Inheritance in Man, Catalog number 190320) has been studied. Several large TDO pedigrees residing throughout the United States have been described, although most of these can be traced back to ancestors who lived in the North Carolina, Virginia, Tennessee triangle area (1–4). There is considerable variation in the clinical expression of TDO (1, 4–9). Taurodontism (elongation of the dental pulp chamber) of the primary and permanent dentition and enamel hypoplasia are fully penetrant features observed in all affected TDO individuals. Eighty-five percent of affected TDO members are born with kinky, curly hair which in half of the cases straightens over time. Dental abscesses are common (observed in 80% of affected individuals), and result from the wearing of the hypoplastic enamel and subsequent exposure of the large dental pulp chamber. Because of the high frequency of abscesses, 40% of affected TDO adults are edentulous. Cranial thickening and obliteration of the frontal and mastoid sinuses are observed in 65–80% of affected individuals and appears to progress with age. Several other clinical features including macrocephaly, dolicocephaly, a high prevalence of dental caries, narrowing of the ear canal, altered craniofacial morphology, and fingernail involvement have been described in TDO patients.

Early in embryological development, murine dlx and msx genes are expressed in distinct and overlapping regions of the first and second branchial arches (11–17). These tissues give rise to many structures including hair, teeth, and bone. Targeted disruption of mouse msx1 results in complete absence of incisors and arrested molar development (18).

Similarly, mutations in human MSX1 were found to cause selective tooth agenesis (19). In mice, msx2 is expressed in the bone forming regions of the mandible, maxilla, and the developing cranial sutures (11), while mutations in human MSX2 cause autosomal dominant craniosynostosis, Boston type, a disease manifesting premature closure of the cranial sutures (20).

The function of dlx genes, although less well characterized than msx genes, is being investigated in numerous species including mouse, rat, zebrafish, and Xenopus (17, 21–26). Recent studies using dlx1-/- and/or dlx2-/- null mutant mice reveal the importance of distal-less gene expression in normal craniofacial development and the development of normal dentition (16). An absence of dlx1 and/or dlx2 affects a number of tissues derived from the proximal first and second branchial arches including cartilage and bones of the face and ear. In development of the teeth, the single mutants (dlx1-/- or dlx2-/-) had apparently normal dentition, whereas the double mutant (dlx1-/-dlx2-/-) exhibited absence of maxillary molars.

In humans, five DLX genes have been cloned and localized. DLX1 and DLX2 are located on chromosome 2q32 near the HOXD cluster (27), DLX5 and DLX6 are located on chromosome 7q22 on the opposite arm of the HOXA cluster (15), and DLX7 is located on chromosome 17, 1–2 Mb from the HOXB cluster (28). Although the cloning has not been previously reported, DLX3 has putatively been localized to chromosome 17 near DLX7 (28).

The present invention describes the linkage of TDO to a 7 centiMorgan region (D17S932–D17S941) of chromosome 17 in four North Carolina families (29). A maximum multipoint lod score of 11.41 was observed at D17S941 (theta= 0.00) with no indication of genetic heterogeneity. Because DLX7 and putatively DLX3 reside in this region, both genes were examined as possible candidates for the TDO syndrome.

The genomic cloning and sequencing of both human DLX7 and DLX3, and the identification of a common mutation in DLX3 present in all affected members of six TDO pedigrees is described herein.

I. Preparation of DLX3-Encoding Nucleic Acid Molecules, DLX3 Proteins, and Antibodies Thereto
A. Nucleic Acid Molecules Nucleic acid molecules encoding the DLX proteins of the invention may be prepared by two general methods: (1) They may be synthesized from appropriate nucleotide triphosphates, or (2) they may be isolated from biological sources. Both methods utilize protocols well known in the art.

The availability of nucleotide sequence information, such as the full length cDNA having Sequence I.D. No. 1 or Sequence I.D. No. 3, enables preparation of an isolated nucleic acid molecule of the invention by oligonucleotide synthesis. Synthetic oligonucleotides may be prepared by the phosphoramadite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a 1.6 kb double-stranded molecule may be synthesized as several smaller segments of appropriate complementarity. Complementary segments thus produced may be ligated such that each segment possesses appropriate cohesive termini for attachment of an adjacent segment. Adjacent segments may be ligated by annealing cohesive termini in the presence of DNA ligase to construct an entire 1.6 kb double-stranded molecule. A synthetic DNA molecule so constructed may then be cloned and amplified in an appropriate vector.

Nucleic acid sequences encoding DLX3 proteins may be isolated from appropriate biological sources using methods known in the art. In a preferred embodiment, a cDNA clone is isolated from an expression library of human origin. In an alternative embodiment, genomic clones encoding DLX3 may be isolated. Alternatively, cDNA or genomic clones encoding DLX3 from other animal species may be obtained.

In accordance with the present invention, nucleic acids having the appropriate level of sequence homology with the protein coding region of Sequence I.D. Nos. 1 or 2 may be identified by using hybridization and washing conditions of appropriate stringency. For example, hybridizations may be performed, using a hybridization solution comprising: 5×SSC, 5×Denhardt's reagent, 1.0% SDS, 100 µg/ml denatured, fragmented salmon sperm DNA, 0.05% sodium pyrophosphate and up to 50% formamide. Hybridization is carried out at 37–42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes–1 hour at 37° C. in 1×SSC and 1% SDS; (4) 2 hours at 42–65° C. in 1×SSC and 1% SDS, changing the solution every 30 minutes.

One common formula for calculating the stringency conditions required to achieve hybridization between nucleic acid molecules of a specified sequence homology is as follows (Sambrook et al., 1989):

$$T_m = 81.5° C. + 16.6 \text{ Log } [Na+] + 0.41(\% \text{ G+C}) - 0.63(\% \text{ formamide}) - 600/\#bp \text{ in duplex}$$

As an illustration of the above formula, using [N+]=[0.368] and 50% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C.

Nucleic acids of the present invention may be maintained as DNA in any convenient cloning vector. In a preferred embodiment, clones are maintained in plasmid cloning/ expression vector, such as pBluescript (Stratagene, La Jolla, Calif.), which is propagated in a suitable E. coli host cell.

The nucleic acids of the invention may also be used as starting materials for site-directed mutagenesis. Such mutations may give rise to DLX3 proteins of increased therapeutic efficacy.

DLX3-encoding nucleic acid molecules of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention, such as selected segments of the cDNA having Sequence I.D. No. 1 or Sequence I.D. No. 3. Such oligonucleotides are useful as probes for detecting or isolating dlx3 genes in other species.

B. Proteins

A full-length DLX3 protein of the present invention may be prepared in a variety of ways, according to known methods. The protein may be purified from appropriate sources, e.g., animal cultured cells or tissues, by immunoaffinity purification. However, this is not a preferred method due to the low amount of protein likely to be present in a given cell type at any time.

The availability of nucleic acids molecules encoding DLX3 enables production of the protein using in vitro expression methods known in the art. For example, a cDNA or gene may be cloned into an appropriate in vitro transcription vector, such as pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech, Madison, Wis. or BRL, Rockville, Md.

Alternatively, according to a preferred embodiment, larger quantities of DLX3 or DLX3Δ may be produced by expression in a suitable procaryotic or eucaryotic system. For example, part or all of a DNA molecule, such as the cDNA having Sequence I.D. No. 1, may be inserted into a plasmid vector adapted for expression in a bacterial cell, such as E. coli, or into a baculovirus vector for expression in an insect cell. Such vectors comprise the regulatory elements necessary for expression of the DNA in the host cell (e.g. E. coli or insect cell), positioned in such a manner as to permit expression of the DNA in the host cell. Such regulatory elements required for expression include promoter sequences, transcription initiation sequences and, optionally, enhancer sequences.

The DLX3 proteins or derivatives thereof produced by gene expression in a recombinant procaryotic or eucyarotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6–8 histidine residues at their N-terminus or C-terminus. Such methods are commonly used by skilled practitioners.

The DLX3 proteins of the invention, prepared by the aforementioned methods, may be analyzed according to standard procedures. For example, such proteins may be subjected to amino acid sequence analysis, according to known methods.

The present invention also provides antibodies capable of immunospecifically binding to proteins of the invention. Polyclonal antibodies directed toward DLX3 may be prepared according to standard methods. In a preferred embodiment, monoclonal antibodies are prepared, which react immunospecifically with various epitopes of DLX3. Monoclonal antibodies may be prepared according to general methods of Köhler and Milstein, following standard protocols. Polyclonal or monoclonal antibodies that immunospecifically interact with DLX3 can be utilized for identifying and purifying such proteins. For example, antibodies may be utilized for affinity separation of proteins with which they immunospecifically interact. Antibodies may also be used to immunoprecipitate proteins from a sample containing a mixture of proteins and other biological molecules. Other uses of anti-DLX3 antibodies are described below.

II. Uses of DLX3-Encoding Nucleic Acids, DLX3 Proteins and Antibodies Thereto

The potential of recombinant genetic engineering methods to provide novel therapeutic reagents has received considerable attention in recent years. Protocols are currently available for the stable introduction and expression of genes encoding the DLX3 proteins disclosed herein. The present invention provides nucleic acid sequences which, upon stable introduction into a recipient cell express DLX3 proteins which may be purified and used to augment bone growth and regeneration. The DLX3 encoding nucleic acids of the invention may also be used to advantage in diagnostic and genetic screening assays to identify those individuals at risk for TDO. Additionally, they may be used for prenatal screening. Finally, DLX3 proteins of the invention may be used as a research tool to identify other proteins, factors or chemical reagents that are intimately involved in osseous repair, regeneration and regrowth.

For administration of the DLX3 encoding nucleic acids or proteins to patients, the DNA or protein may be complexed in a liposome preparation. The liposomes may be further complexed with monoclonal antibodies specific for a pre-determined target cell to facilitate cell specific targeting of the DLX3 based reagents of the present invention.

A. DLX3-Encoding Nucleic Acids

DLX3-encoding nucleic acids may be used for a variety of purposes in accordance with the present invention. DLX3-encoding DNA, RNA, or fragments thereof may be used as probes to detect the presence of and/or expression of genes encoding DLX3 proteins. Methods in which DLX3-encoding nucleic acids may be utilized as probes for such assays include, but are not limited to: (1) in situ hybridization; (2) Southern hybridization (3) northern hybridization; (4) assorted amplification reactions such as polymerase chain reactions (PCR) and (5) genetic and diagnostic screening assays.

The DLX3-encoding nucleic acids of the invention may also be utilized as probes to identify related genes from other species. As is well known in the art, hybridization stringencies may be adjusted to allow hybridization of nucleic acid probes with complementary sequences of varying degrees of homology. Thus, DLX3-encoding nucleic acids may be used to advantage to identify and characterize other genes of varying degrees of relation to DLX3Δ, thereby enabling further characterization of the signalling cascade involved in the growth, repair and regeneration of bone. Additionally, they may be used to identify genes encoding proteins that interact with DLX3 (e.g., by the "interaction trap" technique), which should further accelerate elucidation of these cellular signalling mechanisms.

Nucleic acid molecules, or fragments thereof, encoding DLX3 may also be utilized to control the production of DLX3, thereby regulating the amount of protein available to participate in bone growth, repair and regeneration signalling pathways.

In one embodiment, the nucleic acid molecules of the invention or variant forms thereof may be used to decrease expression of DLX3Δ. In this embodiment, antisense molecules are employed which are targeted to DLX3Δ-encoding genes. The use of antisense molecules to decrease expression levels of a pre-determined gene is known in the art.

Overproduction of DLX3 in transfected cells may be assessed by immunofluorescence or any other standard technique known in the art. Alternatively, overexpression of DLX3 by this method may facilitate the isolation and characterization of other components involved in the protein-protein complex formation that occurs during bone regeneration and repair.

As described above, DLX3-encoding nucleic acids are also used to advantage to produce large quantities of substantially pure DLX3 protein, or selected portions thereof. Finally, the availablity of the complete coding region for DLX3 proteins provides reagents for site-directed mutagenesis to generate proteins with differing biological activities.

B. DLX3 Protein and Antibodies

Purified DLX3, or fragments thereof, may be used to produce polyclonal or monoclonal antibodies which also may serve as sensitive detection reagents for the presence and accumulation of DLX3 (or complexes containing DLX3) in cultured cells. Recombinant techniques enable expression of fusion proteins containing part or all of the DLX3 protein. The full length protein or fragments of the protein may be used to advantage to generate an array of monoclonal antibodies specific for various epitopes of the protein, thereby providing even greater sensitivity for detection of the protein in cells.

Polyclonal or monoclonal antibodies immunologically specific for DLX3 may be used in a variety of assays designed to detect and quantitate the protein. Such assays include, but are not limited to: (1) flow cytometric analysis; (2) immunochemical localization of DLX3 in cells; and (3) immunoblot analysis (e.g., dot blot, Western blot) of extracts from various cells. Additionally, as described above, anti-DLX3 can be used for purification of DLX3 (e.g., affinity column purification, immunoprecipitation).

From the foregoing discussion, it will be appreciated that DLX-encoding nucleic acids, DLX3 expressing vectors, DLX proteins and anti-DLX antibodies of the invention can be used to detect DLX3 gene expression and alter DLX protein accumulation for purposes of assessing the genetic and protein interactions involved in osseous growth, development, regeneration and repair.

The definitions set forth below are provided to facilitate understanding of the subject matter of the present invention:

With reference to nucleic acids of the invention, the term "isolated nucleic acid" is sometimes used. This term, when applied to DNA, refers to a DNA molecule that is separated from sequences with which it is immediately contiguous (in the 5' and/or 3' directions) in the naturally occurring genome of the organism from which it was derived. For example, the "isolated nucleic acid" may comprise a DNA molecule inserted into a vector, such as a plasmid or virus vector, or integrated into the genomic DNA of a procaryote or eucaryote. Recombinant plasmids or vectors containing novel DLX3 genes that may be propagated in *E. coli, S. cerevisiae, S. pombe*, baculovirus and mammalian or insect tissue culture cells are contemplated for use in the present invention. These vectors may optionally contain strong constitutive promoter elements to facilitate high expression of the DLX genes of the invention. Alternatively, they may contain inducible promoter elements so that expression of the DLX3 genes of the invention can be controlled by addition of an inducer compound.

The term "natural allelic variants" is used herein to refer to various specific nucleotide sequences and variants thereof that would occur in a human population. The usage of different wobble codons and genetic polymorphisms which give rise to conservative or neutral amino acid substitutions in the encoded protein are examples of such variants. Additionally, the term "substantially complementary" refers to oligo sequences that may not be perfectly matched to a target sequence, but the mismatches do not materially affect the ability of the oligo to hybridize with its target sequence under the conditions described.

The term "selectable marker gene" refers to a gene product that when expressed confers a selectable phenotype such as antibiotic resistance on a transformed cell.

With respect to RNA molecules of the invention, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to protein, the term "isolated protein" or "isolated and purified protein" is sometimes used herein. This term refers primarily to a protein produced by expression of an isolated nucleic acid molecule of the invention. Alternatively, this term may refer to a protein which has been sufficiently separated from other proteins with which it would naturally be associated, so as to exist in "substantially pure" form.

The term "substantially pure" refers to a preparation comprising at least 50–60% by weight the compound of interest (e.g., nucleic acid, oligonucleotide, protein, etc.). More preferably, the preparation comprises at least 75% by weight, and most preferably 90–99% by weight, of the compound of interest. Purity is measured by methods appropriate for the compound of interest (e.g. chromatographic methods, agarose or polyacrylamide gel electrophoresis, HPLC analysis, and the like).

Proteins may be expressed in desired cell types to high levels and purified using conventional methods. Following purification, proteins may be lyophilized and stored for long periods.

With respect to antibodies of the invention, the term "immunologically specific" refers to antibodies that bind to one or more epitopes of a protein of interest (e.g., DLX3), but which do not immunospecifically recognize and bind other molecules in a sample containing a mixed population of antigenic biological molecules.

With respect to oligonucleotides, the term "specifically hybridizing" refers to the association between two single-stranded nucleotide molecules of sufficiently complementary sequence to permit such hybridization under predetermined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "promoter region" refers to the 5' regulatory regions of a gene. In the present invention, the use of both strong constitutive gene promoters and inducible gene promoters is contemplated. An exemplary 5' region of the present invention is provided in Sequence I.D. No. 5. See FIG. 6.

The term "operably linked" indicates that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The term "DNA construct" refers to a genetic sequence in a form adapted to transform cells. These constructs may be administered to cells in a viral or plasmid vector. Other methods of delivery such as electroporation, polyethylene glycol mediated transformation and calcium phosphate precipitation are also contemplated to be within the scope of the present invention. Standard methods for delivery of DNA and protocols for preparing the transforming DNA may be found in *Current Protocols in Molecular Biology*, eds. Frederick M. Ausubel et al., John Wiley & Sons, 1995.

The nucleic acids, proteins and antibodies of the present invention are useful as research tools and will facilitate the elucidation of the mechanistic action of the novel genetic and protein interactions involved in osseous growth, development, repair and regeneration. They should also find broad application in the elucidation of the signal transduction pathway directing bone growth and regeneration.

The following specific examples are provided to illustrate embodiments of the invention. They are not intended to limit the scope of the invention in any way.

EXAMPLE I

Identification of a Mutation in DLX3 Associated with TDO Syndrome

To identify genes involved in craniofacial development, the TDO syndrome has been investigated. The cloning and characterization of the DLX3 gene and its mutated counterpart, involved in this disorder is described hereinbelow.

The following methods are provided to facilitate practice of the present invention.

DNA Analysis

Total genomic DNA was isolated from lymphoblasts or buccal swabs of all TDO family members and North Carolina controls as previously described (5).

Radiation Hybrid Mapping

Each polymorphic marker used in linkage analysis was typed by PCR on the G3 and TNG3 whole genome radiation hybrid panels (Research Genetics, Huntsville, Ala.). Retention patterns were analyzed using the RHMAP version 3.0 program package (33). Two point lod scores between markers were determined and a framework map based on the genetic order of the polymorphic markers was built using the RHMAXLIK program. DLX7 was placed within the framework map using primers DLX7ex2F and DLX7ex2R.

PCR Amplification of DLX7

The coding sequence of DLX7 was amplified by PCR using primers designed from the previously published sequence (Genbank accession, Q92988). A 1.6 kb fragment containing exon 1, exon 2 and the intervening intron was amplified using forward primer (DLX7F) 5'-GCTCACGGACCCATACGAGT-3' (SEQ. ID NO: 6) and the reverse primer (DLX7R) 5'-CAAGGAAAAATCGCTGGGTGG-3' (SEQ. ID NO: 7). PCR was performed in 50 µL reactions containing 100 ng genomic DNA, 10 mM TrisHCl (pH 8.2), 1.5 mM $MgCl_2$, 50 mM KCl, 0.2 mM dNTPs, 0.5 µM each primer, 5% DMSO, 2U Taq Extender (Stratagene, La Jolla, Calif.) and 2U Taq polymerase. The reaction mixture was denatured for 5 minutes at 95° C. after which Taq polymerase was added. The reaction mixture was then cycled 35 times at 94° C. for 1 minute, 59° C. for 1 minute, and 72° C. for 5 minutes and followed by a final extension at 72° C. for 5 minutes. The PCR product was gel purified and the DNA was isolated by Wizard PCR preps (Promega, Madison, Wis.). Exon 1 was sequenced using the primers DLX7F and DLX7ex1R (5'-GCCACAGCACCAATCCATC-3'; SEQ. ID NO: 8). Exon 2 was sequenced using primers DLX7ex2F (5'-GCTAGACAGGGAGACATGG-3'; SEQ. ID NO: 9) and DLX7ex2R (5'-CCCATCTGGAGCTGGTTTC-3'; SEQ. ID NO: 10). Sequencing was performed by the Wake Forest University Medical Center Sequencing Core facility using a Prism 377 automated sequencer (Applied Biosystems, Foster City, Calif.).

Cloning and Sequencing of Human DLX3

Bacterial artificial chrosome (BAC) clones 526014 and 535K4 were isolated from the human BAC library version III (Research Genetics, Huntsville, Ala.) using DLX7F and DLX7ex1R primers by sequential PCR screening. The BAC clones were digested with BamHI, EcoRI, SmaI, and PstI. The digests were analyzed by electrophoresis through a 1% agarose gel and blotted in duplicate to nylon membranes. One set of membranes was probed with a degenerate oligonucleotide from the 3' end of the homeobox and the second membrane was probed with a degenerate oligonucleotide from the 5' end of the homeobox (28). Two hybridizing bands were observed in all digests, one corresponding to DLX7 as found by probing the same membranes with the 1.6 kb DLX7 PCR fragment (see above), and the other corresponding to the putative DLX3 gene. The putative DLX3 fragments were subcloned and sequenced using overlapping sets of primers from either end using automated sequencing. Both DNA strands of the three exons and two introns were sequenced in their entirety. This sequence was deposited into Genbank (AF028233). Nucleotide and protein sequences were analyzed and compared to known sequences using GCG programs (Madison, Wis.).

Identification of CA/GT Dinucleotide Repeat Polymorphism Associated with DLX3

A dinucleotide repeat polymorphism was identified 440 bp upstream of the putative ATG start site through sequence analysis. The polymorphism was amplified by PCR with primers DLX3F (5'-CTTATCTGGGCTGGAGCTA-3'; SEQ. ID NO: 11) and DLX3R (5'-GCGCTGATTGGCTGCAAGT-3'; SEQ. ID NO: 12). Two point linkage analysis using the four North Carolina families was performed using MLINK program version 5.1 from the LINKAGE computer program package as previously described (29).

Mutation Detection

The DLX3 gene was sequenced in two affected members and two unaffected members of TDO pedigree 1 to search for a mutation. Each exon was amplified individually using primer pairs depicted in FIG. 2. Exon 3 was amplified by PCR using DLX3E3F (FIG. 2) and DLX3E3R 5' CTC-CCATACACCTCACCCG 3' (SEQ. ID NO: 13). The PCR reaction was done as described for DLX7 except that the extension time was shortened to 1 minute and the anneal temperatures were as follows: exon 1 (60° C.), exon 2 (60° C.), and exon 3 (55° C.). The PCR products were purified as above and the nucleotide sequence was determined using the automated sequencer. Additionally, exon 3 PCR products from two affected TDO individuals (Family 1, individuals III-15 and IV-12) were subcloned into pGEM-T (Promega, Madison, Wis.) and 6 individual clones were sequenced which revealed the normal and deleted sequence.

PCR amplification of all members of the TDO pedigrees was carried out using DLX3mut1 and DLX3mut2 (boxed primers in FIG. 2). The normal allele results in a product of 145 nucleotides and the deleted allele is 141 nucleotides. PCR amplification was performed on 50 ng of genomic DNA using 25 pmol of each oligonucleotide and 5 pmol of endlabelled DLX3mut1 in a standard 10 µL reaction. DNA was denatured at 95° C. for five minutes, followed by 30 cycles of denaturation at 94° C. for 40 s, annealing at 58° C. for 40s, and extension at 72° C. for 40s. The PCR products were analyzed by electrophoresis through a 6% denaturing polyacrylamide gel and autoradiography.

Results

Identification of a Common Haplotype in the TDO Region.

Previous reports placed the TDO linkage within a 7cM region of chromosome 17q21 (29). To evaluate the possibility that these families inherited the TDO locus from a common ancestor, the haplotypes inherited in the four North Carolina families with multiple polymorphic markers in the linked region were investigated. A common haplotype in the families was observed for markers D17S941 and D17S943 (FIG. 1), effectively narrowing the TDO candidate region to 5 cM between D17S806 and D17S788 (30). Two additional TDO families (6 affected, 1 unaffected member) from central North Carolina were typed for markers D17S941 and D17S943 and also found to contain this common haplotype. These families were not known to be related to the four families used in the original linkage analysis. Although available, these two families were not used in the original linkage analysis because their small size added little to the analysis. The common haplotype suggests that affected individuals from these six families shared a common genetic region "identical by descent" and revealed an ancestral recombination between D17S806 and D17S943. Each affected member of the six pedigrees carried allele 5 at D17S943 and allele 4 at D17S941. Only genes that mapped to this common haplotype region were considered possible TDO candidate genes.

Mapping of DLX7 to the Common Haplotype Region and Mutational Analysis

Hundreds of expressed sequences, including several candidate genes which could account for the tissue involvement and/or phenotype of TDO, are located in 17q21 (31, 32). To determine whether these candidate genes mapped to the defined common haplotype region, it was necessary to construct a physical map of the region. A radiation hybrid (RH) map of the TDO region was constructed using the Stanford G3 and TNG3 whole genome RH panels (33). Each polymorphic marker used in linkage analysis was typed in both panels to construct a framework map of the TDO region, and STSs from candidate genes were added to this map (data not shown). The human DLX7 gene had been previously mapped to 17q21–22, a region which includes the 5 cM TDO common haplotype interval (28). Using the framework RH map and primers derived from the published sequence, DLX7 locus was further localized to the common haplotype region within 200 kb of D17S943.

To assess the possible roles of distal-less genes in the development of teeth (12, 25, 27), expression of these genes in tissues involved in TDO, and localization of DLX7 to the common haplotype region, DLX7 was further analyzed. The entire DLX7 gene was amplified by PCR from human genomic DNA using primers from the 5' and 3' untranslated regions of the gene according to the above-described methods. The resulting 1.6 kb PCR product consists of two exons separated by a 429 bp intron (GenBank AF028235). The 5' end of the homeodomain is contained in exon 1 while the 3' end is contained in exon 2. Interestingly, murine dlx7 consists of three exons, with the homeodomain residing in exons 2 and 3 (28). The DLX7 gene, including both exons and splice sites, from two affected and two unaffected TDO individuals was sequenced and no mutations were identified.

Cloning, Nucleotide Sequence Analysis, and Chromosomal Location of the Human DLX3 Gene Murine studies indicate that another distal-less homologue, dlx3, resides close to dlx7 (28). The results of physical mapping studies revealed that human DLX3 is located in close proximity to DLX7. Two human BAC clones were isolated using the 3' untranslated region of DLX7 with the hypothesis that these BAC clones would also contain the entire DLX3 gene. Southern blot analysis using degenerate homeobox oligonucleotides as probes indicated that both BAC clones contained two homeobox regions. Subclones containing fragments of the putative DLX3 homeobox region were prepared, and the nucleotide sequence of the flanking and protein coding regions were determined, (GenBank Accession No.: AF028233) See FIG. 2.

The human DLX3 gene consists of three exons with the homeobox contained in exons 2 and 3. Exons 1 and 2 are separated by a 1.1 kb intron; exons 2 and 3 are separated by a 1.6 kb intron. The presence of an inframe stop codon at −158 bp and the absence of other inframe ATG codons is consistent with the assignment of the ATG initiation codon in FIG. 2. Additionally, the sequence surrounding the initiator ATG codon conforms to the consensus Kozak sequence ($^{-9}$GCCGCC[A or G]CC$\underline{AUG}$G$^{+4}$ (SEQ ID NO:25) with 9 out of 13 nucleotides matching the consensus (FIG. 2) (34). The most highly conserved purine (A or G) at position −3 is present in human DLX3 and should be sufficient to direct translation (34). Comparative analysis of the nucleotide and derived amino acid sequences revealed that human DLX3 is more similar to the mouse, zebrafish, axolotl, xenopus, and newt dlx3 than to any other distal-less family members (FIG. 2). Within the homeobox region, the putative DLX3 is 100% identical to mouse, axolotl, newt, zebrafish, and xenopus dlx3. Over the entire protein, DLX3 is 98% identical to mouse dlx3, 77% identical to axolotl dlx3, 75% identical to newt dlx3, 69% identical to zebrafish dlx3, and 67% identical to xenopus dlx3, indicating that it is in fact the human homologue of dlx3. A 2.5 kb DLX3 transcript in human placental RNA has been detected by Northern blot analysis which is the same size transcript detected in mouse embryos (18).

The human DLX3 gene was localized to the common haplotype region using RH mapping. Additionally, the DLX3 gene was sublocalized by flourescent in situ hybridization (FISH) to chromosome 17q20–21 (data not shown). In order to rule out a deletion of the entire DLX3 or DLX7 gene in TDO patients, subclones containing DLX3 alone, DLX7 alone, or both genes were used in FISH analysis of two affected and two unaffected members of TDO pedigree 1. A positive signal was observed on both copies of chromosome 17 for all probes in all individuals indicating a large deletion is not responsible for the TDO phenotype in these individuals.

DLX3 Polymorphism

The nucleotide sequence of DLX3 revealed a CA/GT dinucleotide repeat 440bp upstream from the putative ATG start site (GenBank AF028234). This dinucleotide repeat proved to be highly polymorphic with heterozygosity rates of 0.85 in Caucasians, and 0.90 in African Americans. Two point linkage analysis was performed between the DLX3 polymorphism and TDO in the four North Carolina families used in linkage analysis. A maximum lod score of 9.15 at theta 0.00 was observed using the four North Carolina TDO families studied in the original linkage analysis (29). A common allele was observed in all affected members of these four pedigrees and the two small pedigrees not used in the original linkage analysis, thus placing the marker within the common haplotype region (FIG. 1).

Mutational Analysis of DLX3

Figure 4A:
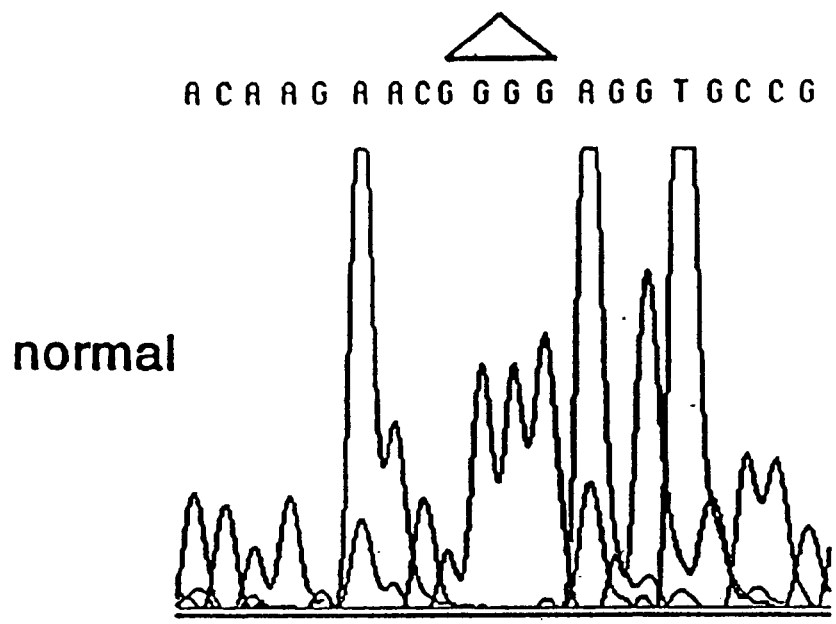
FIG. 4 shows the nucleotide sequence of two cloned alleles from an individual with TDO. The upper panel depicts the normal allele (SEQ ID NO:2). The lower panel shows the deleted allele (SEQ ID NO:4). The overhead triangle indicates the four nucleotides deleted in one allele of affected TDO individuals.
Figure 4B:
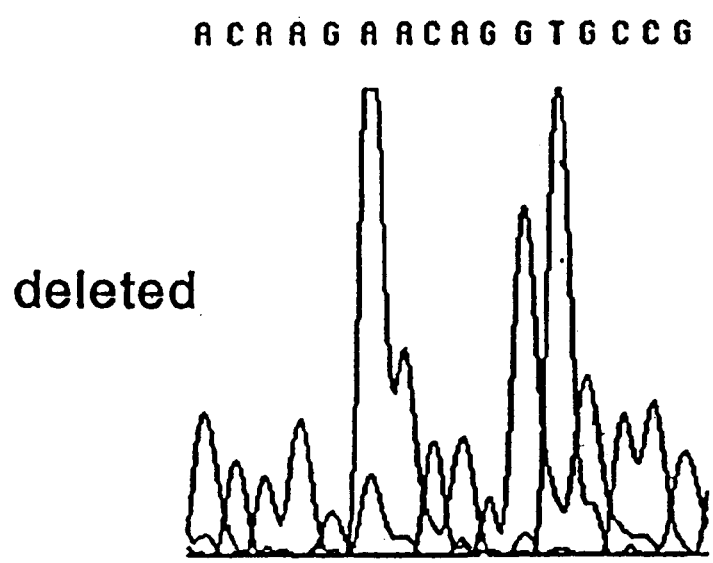

To search for a mutation in DLX3 which might contribute to TDO in these six North Carolina families, we sequenced PCR products from the three exons in two affected members and two unaffected members of pedigree 1. Each exon including flanking sequences was amplified by PCR and sequenced using primers depicted in FIG. 2. We detected a deletion of four G nucleotides in one allele of the two affected members of family 1 (individuals III-15, and IV-12) at nucleotide 3198 (29). The deletion mutation in the two affected members rendered the sequence unreadable in the PCR products; therefore, the products were subcloned. Six individual clones from the two affected members were sequenced, clearly revealing the 4 base pair deletion in one allele, the other allele being normal (FIG. 4). This deletion results in a frameshift of the 3' terminal portion of DLX3 (FIG. 2) but leaves the homeodomain intact. An inframe termination codon is present in the deletion allele at nucleotide 3398; this results in a mutant protein which is 32 amino acids shorter than the normal DLX3 protein. The four base pair deletion was observed in only one copy of the DLX3 gene which is consistent with TDO being inherited as an autosomal dominant disorder.

Members of the TDO pedigrees were analyzed for this DLX3 deletion using PCR (FIG. 5). Primers flanking the deletion (DLX3mut1 and DLX3mut2 in FIG. 2) were used to examine all members of the six North Carolina TDO pedigrees (46 affected, 24 unaffected). All affected TDO individuals carried one copy of DLX3 with the 4 base pair deletion (141 bp) and one normal copy of DLX3 (145 bp). The 24 unaffected individuals only carried the normal 145 bp allele. In addition, 100 unrelated Caucasian controls from North Carolina were tested for the mutation, and none were found that contained this deletion. Taken together, the analysis conducted of members of the TDO families and of unrelated individuals from similar ethnic background showed a complete correlation of the mutant allele with the disease phenotype and strongly suggests that the four base pair deletion in DLX3 is responsible for TDO.

Discussion

The observation that a deletion of four G nucleotides in DLX3 is present in all affected TDO members in six families tends to indicate that this mutation is responsible for TDO. There are several noteworthy reasons supporting this conclusion. First, complete concordance between genotype and disease status in 46 affected and 24 unaffected individuals from these six families was observed. Second, the four base pair deletion found in all affected individuals results in a frameshift and premature termination of the 3' half of the DLX3 protein. This mutation in DLX3 is likely to alter the function of the protein. Third, the expression pattern of dlx3 in mice is highly correlated with the tissues affected in TDO patients.

The most penetrant clinical findings in TDO patients are the presence of taurodontism and enamel defects in teeth. In early murine tooth formation (bud and cap stage), dlx3 is primarily expressed in the neural crest derived mesenchymal component of the tooth that will later give rise to the dentin and pulp (17). However, in the late bell stage, as the inner enamel epithelium and mesenchyme undergo terminal differentiation, dlx3 expression shifts to being predominantly expressed in the inner enamel epithelium and preameloblasts, while the outer enamel epithelium does not show dlx3 expression (17). The inner enamel epithelium gives rise to the ameloblasts that are responsible for enamel formation and this pattern of dlx3 expression is thus consistent with the thin pitted enamel TDO phenotype. Furthermore, the inner enamel epithelium eventually forms Herwigs root sheath which is responsible for establishing root morphology. Failure of Herwigs root sheath to invaginate at an appropriate time results in taurodontism as is seen in TDO. The whisker and hair follicles of mice strongly express dlx3 before birth followed by a decrease in expression after birth. This could correlate to the kinky, curly hair observed in TDO patients at birth, that in over half the cases straightens during infancy. The osseous cranial changes in TDO patients are more difficult to characterize and quantitate than the presence of hair and tooth anomalies, but murine dlx3 expression has been detected in the dense mesenchyme of the branchial arches which subsequently condenses and ossifies to form the bones of the skull and face (17).

The phenotype observed in TDO patients is not as severe as the phenotype observed in dlx1 or dlx2 homozygous null mice (16), although some of the same tissues are affected. One explanation for this difference in phenotypic expression is that TDO patients have one normal allele of DLX3, possibly fulfilling the normal function, whereas the null mutant mice lack expression of dlx1 and/or dlx2. Another explanation for this difference in severity hinges on the overlapping yet distinct expression of the dlx genes. Dlx1 and dlx2 are expressed in the mesenchyme of both proximal and distal region of the branchial arches, yet the phenotype of the null mutants is only observed in proximal derived structures (16). Studies to date indicate that dlx1, 2, 3, 5, 6, and 7 are all expressed in the most distal regions of the first and second branchial arches, whereas only dlx1 and dlx2 are expressed in the proximal portions of these arches. Therefore, it can be envisioned that other dlx proteins are compensating for the absence of dlx1 and dlx2 in the distal derived structures. Although dlx1 and dlx2 have similar spatial and temporal expression patterns, the single null mutants differ considerably suggesting that small differences in expression patterns of the dlx genes can account for different phenotypes. Furthermore, only the double null mutants (dlx1–/– dlx2–/–) exhibited a tooth phenotype, implying that dlx1 and 2 can compensate for the loss of one another.

Recently, another homeobox gene, REIG1, has been implicated in Reiger syndrome, a disease affecting multiple tissues including the eyes, teeth, and umbilical cord (35). Dental findings include enamel hypoplasia, conical and misshapen teeth, hypodontia, and impactions (35). Of the six mutations identified in the REIG1 gene, five were found within the homeodomain. The sixth mutation produced premature termination of the REIG1 protein 34 amino acids distal to the homeodomain, thus altering the C-terminal region of the protein (35). While the mutation in DLX3 presented here does not occur within the homeobox region, the 3' half of the protein would be affected by the deletion. Two mechanisms could account for the dominant TDO phenotype. First, the mutation could act as a gain of function mutation. For example, the mutant DLX3 protein might bind to specific DNA sequences but not activate transcription; or the mutant DLX3 could interact with other transcription factors or the transcription machinery resulting in functional inactivity. Alternatively, haploinsufficiency could account for the TDO phenotype if genes that are activated/repressed or interacting with DLX3 are highly sensitive to the amount of DLX3 in the cell. Analysis of the DLX3 frameshift mutant could help elucidate the consequences of this mutation on DLX3 structure, protein interactions, DNA binding, and activation/repression of transcription.

This report of a human mutation in a DLX gene provides insight into the importance of DLX3 in the development of dentition as well as normal craniofacial development. The most penetrant clinical findings associated with TDO, taurodontism and enamel hypoplasia, affect both the primary and permanent dentition. The variable osseous changes occur well into adulthood implying that DLX3 is expressed early in development, and possibly normal or mutant DLX3 is expressed throughout life. An increased understanding of how DLX3 functions, together with additional assessment of tissue specific and temporal expression of vertebrate DLX3 may increase our understanding of the effects of the mutated human DLX3 in TDO and also help define the roles of the distal-less genes in craniofacial and odontogenic development.

Example II

Genetic Testing of Patients for the Presence of DLX3 Mutations

As described in Example I, a four nucleotide deletion in the DLX3 gene is present in TDO patients. The availability of the nucleic acids having the sequence of Sequence I.D. Nos. 1 and 3 as well as the PCR primer sets set forth in Example I provide reagents for genetic testing in patients for the presence of absence of the DLX3 mutation described herein.

DNA may be isolated from either blood or buccal swabs. For a DNA isolation from the cheek, a buccal swab is obtained. The swab is immersed in 600 microliters of 50 mM NaOH in a 1.5 ml eppendorf tube. The tube is then vortexed for 10 seconds followed by a 5 minute incubation in a 95 degree hot water bath. Following this incubation, 60 microliters of Tris (1 mM, pH 8.0) is added to the tube and the sample vortexed for an additional 10 seconds. The tube is centrifuged in a microfuge for 1 minute to pellet the DNA. The supernatant is then discarded and the sample frozen or the DNA processed for PCR as described above in Example I. Following DNA amplification, the DNA is sequenced in an automated DNA sequencer to confirm the results obtained with PCR.

REFERENCES

1. Kula, K., Hall, K. I., Hart, T. C., Wright, J. T. (1997) Craniofacial morphology of the tricho-dento-osseous syndrome. *Clin. Genet.* 50, 446–454.
2. Wright, J. T., Roberts, M. W., Wilson, A. S., Kudhail, K. (1994) Tricho-dento-osseous syndrome: features of the hair and Teeth. *Oral Surg., Oral Med., Oral Path.* 77, 487–493.
3. Lichtenstein, J., Warson R., Jorgenson, R., Dorst, J. P. McKusick, V. A. (1972) The tricho-dento-osseous (TDO) syndrome. *Amer. J. Hum. Genet.* 24, 569–582.
4. Quattromani, F. L., Shapiro, S. D., Young, R. S., Jorgenson, R. J., Parker, J. W., Blumhardt, R., Reece, R. R. (1983) Clinical heterogeneity in the tricho-dento-osseous syndrome. *Hum. Genet.* 64, 116–121.
5. Wright, J. T., Hall, K. I., Kula, K., Hart, T. C. (1997) Analysis of the tricho-dento-osseous syndrome genotype and phenotype. *Amer. J. Med. Genet.* 72, 197–204.
6. Jorgenson, R. J., Warson, R. W. (1973) Dental abnormalities in the tricho-dento-osseous syndrome. *Oral Surg.* 36, 693–700.
7. Ogden, G. R. (1988) Tricho-dento-osseous syndrome. *Ann. Dent.* 46, 12–14.
8. Seow, W. K. (1993) Trichodentoosseous (TDO) syndrome: case report and literature review. *J. Ped. Dent.* 15, 355–361.
9. Shapiro, S. D., Quattromani, F. L., Jorgenson, R. J., Young, R. S. (1983) Tricho-dento-osseous syndrome: heterogeneity or clinical variability. *Am. J. Med. Genet.* 16, 225–236.
10. Maas, R., Bei, M. (1997) The genetic control of early tooth development. *Crit. Rev. Oral. Biol. Med.* 8, 4–39.
11. MacKenzie, A., Ferguson, M. W. J., Sharpe, P. T. (1992) Expression patterns of the homeobox gene, hox-8, in the mouse embryo suggest a role in specifying tooth initiation and shape. *Development* 115, 403–420.
12. Sharpe, P. T. (1995) Homeobox genes and orofacial development. *Conn. Tiss. Res.* 32, 17–25.
13. Jowett, A. K., Vainio, S., Ferguson, M. W. J., Sharpe, P. T., Thesleff, I. (1993) Epithelial-mesemchymal interactions are required for msx 1 and msx 2 gene expression in the developing murine molar tooth. *Development* 117, 461–470.
14. Thomas, B. L., Porteus, M. H., Rubenstein, J. L. R., Sharpe, P. T. (1995) The spatial localization of Dlx-2 during tooth development. *Conn. Tiss. Res.* 32, 27–34.
15. Simeone, A., Acampora, D., Pannese, M., d'Esposito, M., Stornaiuolo, A., Gulisano. M., Mallamaci, A., Kastury, K., Druck, T., Huebner, K., Boncinelli, E. (1994) Cloning and characterization of two members of the vertebrate Dlx gene family. *Proc. Natl. Acad. Sci. USA* 91, 2250–2254.
16. Qui, M., Bulfone, A., Ghattas, I., Meneses, J., Christensen, L., Sharpe, P. T., Presley, R., Pedersen, R. A., Rubenstein, J. L. R. (1997) Role of the Dlx homeobox genes in proximodistal patterning of the branchial arches: mutations of Dlx-1, Dlx-2, and Dlx-1 and -2 alter morphogenesis of proximal skeletal and soft tissue structures derived from the first and second arches. *Devel. Biol.* 185, 165–184.
17. Robinson, G. W., Mahon, K. A. (1994) Differential and overlapping expression domains of Dlx-2 and Dlx-3 suggest distinct roles for Distal-less homeobox genes in craniofacial development. *Mech. Devel.* 48, 199–215.
18. Satokata, I., Maas, R. (1994) Msx1 deficient mice exhibit cleft palate and abnormalities of craniofacial and tooth development. *Nat. Genet.* 6, 348–356.
19. Vastardis, H., Karimbux, N., Guthua, S. W., Seidman, J. G., Seidman, C. E. (1996) A human MSX1 homeodomain missense mutation causes selective tooth agenesis. *Nat. Genet.* 13, 417–421.
20. Jabs, E. W., Muller, U., Li, X., Ma, L., Luo, W., Haworth, I. S., Klisak, I., Sparkes, R., Warman, M. L., Mulliken, J. B., Snead, M. L., Maxson, R. (1993) A mutation in the homeodomain of the human MSX2 gene in a family affected with autosomal dominant craniosynostosis. *Cell* 75, 443–450.
21. Akimenko, M.-A., Ekker, M., Wegner, J., Lin, W., Westerfield, M. (1994) Combinatorial expression of three zebrafish genes related to Distal-Less: part of a homeobox gene code for the head. *J. Neuroscience.* 14, 3475–3486.
22. Dirksen, M.-L., Morasso, M. I., Sargent, T. D., Jamrich, M. (1994) Differential expression of a Distal-less homeobox gene Xdll-2 in ectodermal cell lineages. *Mech. Devel.* 46, 63–70.
23. McGinnis, W., Krumlauf, R. (1992) Homeobox genes and axial patterning. *Cell* 68, 283–302.
24. Papalpulu, N., Kintner, C. (1993) Xenopus Distal-less related homeobox genes are expressed in the developing forebrain and are induced by planar signals. *Development* 117, 961–975.
25. Weiss, K. M., Bollekens, J., Ruddle, F. H., Takshita, K. (1994) Distal-Less and other homeobox genes in the development of the dentition. *J. Exper. Zoology* 270, 273–284.
26. Weiss, K. M., Ruddle, F. H., Bollekens, J. (1995) Dlx and other homeobox genes in the morphological development of the dentition. *Conn. Tiss. Res.* 32, 35–40.
27. McGuiness, T., Porteus, M. H., Smiga, S., Bulfone, A., Kingsley, C., Qiu, M., Liu, J. K., Long, J. E., Xu, D., Rubenstein, J. L. R. (1996) Sequence, organization, and transcription of the Dlx-1 and Dlx-2 locus. *Genomics* 35, 473–485.
28. Nakamura, S., Stock. D. W., Wydner, K. L., Bollekens, J. A., Takeshita, K., Nagai, B. M., Chiba, S., Kitamura, T., Freeland, T. M., Zhao, Z., Minowada, J., Lawrence, J. B., Weiss, K. M., Ruddle, R. H. (1996) Genomic analysis of a new mammalian distal-less gene: Dlx7. *Genomics* 38, 314–324.
29. Hart, T. C., Bowden, D. W., Bolyard, J., Kula, K., Hall, K., Wright, J. T. (1997) Genetic linkage of the tricho-dento-osseous syndrome to chromosome 17q21. *Hum. Mol. Genet.* 6, 2279–2284.
30. Dib, C, Faure, S., Fizames, C., Samson, D., Drouot, N., Vignal, A., Millasseau, P., Marc, S., Hazan, J., Seboun, E., Lathrop, M., Gyapay, G., Morissette, J., Weissenbach, J. (1996) A Comprehensive genetic map of the human genome based on 5,264 microsattelites. *Nature* 280, 152–154.
31. Hudson, T. J., Stein, J. K., Gerety, S. S., Ma, J., Castle, A. B., Silva, J., Slonim, D. K., Gruglyak, B. R., Xu, SH., et al (1995) An STS-based map of the human genome. *Science* 270, 1945–1954.

32. Stewart, E. A., McKusick, K. B., Aggarwal, A., Bajorek, E., Brady, S., Chu, A., Fang, N., Hadley, D., Harris, M., Hussain, S. et al (1997) An STS-based radiation hybrid map of the human genome. *Genome Res.* 7, 422–433.
33. Lunetta, K. L., Boehnke, M., Lange, K., Cox, D. R. (1996) Selected locus and multiple panel models for radiation hybrid mapping. *Am. J. Hum. Genet.* 59, 717–725.
34. Kozak, M. (1986) Point mutations define a sequence flanking the AUG initiator codon that modulates translation by eukaryotic ribosomes. *Cell* 44, 283–292.
35. Semina, E. V., Reiter, R., Leysens, N. J., Alward, W. L., Small, K. W., Datson, N. A., Siegel-Bartelt, J., Bierke-Nelson, D., Bitoun, P., Zabel, B. U., Carey, J. C., Murray, J. C. (1996) Cloning and characterization of a novel bicoid-related homeobox transcription factor gene, RIEG, involved in Reiger syndrome. *Nat. Genet.* 14, 392–399.

While certain preferred embodiments of the present invention have been described and specifically exemplified above, it is not intended that the invention be limited to such embodiments. Various modifications may be made to the present invention without departing from the scope and spirit thereof, as set forth in the following claims.

What is claimed is:

1. An isolated, human nucleic acid molecule comprising SEQ ID NO: 3, said nucleic acid molecule encoding a DLX3Δ protein, said DLX3Δ protein comprising a homeobox domain.

2. The nucleic acid molecule of claim 1, which is DNA.

3. The DNA molecule of claim 2, which is a cDNA comprising a sequence approximately 2.5 kilobases in length that encodes a truncated human DLX3Δ protein.

4. The DNA molecule of claim 2, which is a gene comprising intron and exons, said gene being located between loci p17S806 and D17S788 on chromosome 17, the exons of said gene comprising the nucleic acid of SEQ ID NO: 3, said gene having a promoter sequence of SEQ ID NO: 5 and said exons encoding said DLX3Δ protein.

5. The isolated nucleic acid molecule of claim 1, further comprising the nucleotide sequence of SEQ ID NO: 5.

6. An isolated nucleic acid molecule consisting of an RNA transcribed from SEQ ID NO: 3, wherein the isolated nucleic acid molecule specifically hybridizes to SEQ ID NO: 3.

7. An isolated nucleic acid molecule comprising a sequence selected from the group consisting of:
   a) SEQ ID NO: 3; and
   b) a sequence encoding the polypeptide of SEQ ID NO: 4.

8. An isolated nucleic acid molecule encoding a DLX3Δ protein of SEQ ID NO: 4.

9. An isolated nucleic acid molecule which is the complement of SEQ ID NO:3.

10. An isolated nucleic acid molecule consisting of the nucleotide sequence of SEQ ID NO: 5.

* * * * *

SEQUENCE LISTING

<160> NUMBER OF SEQ ID NOS: 25

<210> SEQ ID NO 1
<211> LENGTH: 864
<212> TYPE: DNA
<213> ORGANISM: Homo sapiens

<400> SEQUENCE: 1

```
atgagtggct ccttcgatcg caagctcagc agcatcctca ccgacatctc cagctccctt      60
agctgccatg cgggctccaa ggactcgcct accctgcccg agtcttctgt cactgacctg     120
ggctactaca gcgctcccca gcacgattac tactcgggcc agccctatgg ccagacggtg     180
aaccnctaca cctaccacca ccaattcaat ctcaatgggc ttgcaggcac gggcgcttac     240
tcgcccaagt cggaatatac ctacggagcc tcctaccggc aatacggggc gtatcgggag     300
cagccgctgc agcccagga cccagtgtcg gtgaaggagg agccggaagc agaggtgcgc     360
atggtgaatg ggaagcccaa gaaggtccga aagccgcgta caatctactc cagctaccag     420
ctggccgccc tgcagcgccg cttccagaag gcccagtacc tggcgctgcc cgagcgcgcc     480
gagctggccg cgcagctggg cctcacgcag acacaggtga aaatctggtt ccagaaccgc     540
cgttccaagt tcaagaaact ctacaagaac ggggaggtgc cgctggagca cagtcccaat     600
aacagtgatt ccatggcctg caactcacca ccatcacccg ccctctggga cacctcttcc     660
cactccactc cggcccctgc ccgcagtcag ctgccccgc cgctcccata cagtgcctcc     720
cccagctacc tggacgaccc caccaactcc tggtatcacg cacagaacct gagtggaccc     780
cacttacagc agcagccgcc tcagccagcc accctgcacc atgcctctcc cgggccccg     840 cccaaccctg gggctgtgta ctga                                            864
```

<210> SEQ ID NO 2
<211> LENGTH: 287
<212> TYPE: PRT
<213> ORGANISM: Homo sapiens

<400> SEQUENCE: 2

```
Met Ser Gly Ser Phe Asp Arg Lys Leu Ser Ser Ile Leu Thr Asp Ile
1               5                   10                  15

Ser Ser Ser Leu Ser Cys His Ala Gly Ser Lys Asp Ser Pro Thr Leu
            20                  25                  30

Pro Glu Ser Ser Val Thr Asp Leu Gly Tyr Tyr Ser Ala Pro Gln His
        35                  40                  45

Asp Tyr Tyr Ser Gly Gln Pro Tyr Gly Gln Thr Val Asn Pro Tyr Thr
    50                  55                  60

Tyr His His Gln Phe Asn Leu Asn Gly Leu Ala Gly Thr Gly Ala Tyr
65                  70                  75                  80
```

```
Ser Pro Lys Ser Glu Tyr Thr Tyr Gly Ala Ser Tyr Arg Gln Tyr Gly
                85                  90                  95
Ala Tyr Arg Glu Gln Pro Leu Pro Ala Gln Asp Pro Val Ser Val Lys
            100                 105                 110
Glu Glu Pro Glu Ala Glu Val Arg Met Val Asn Gly Lys Pro Lys Lys
        115                 120                 125
Val Arg Lys Pro Arg Thr Ile Tyr Ser Ser Tyr Gln Leu Ala Ala Leu
    130                 135                 140
Gln Arg Arg Phe Gln Lys Ala Gln Tyr Leu Ala Leu Pro Glu Arg Ala
145                 150                 155                 160
Glu Leu Ala Ala Gln Leu Gly Leu Thr Gln Thr Gln Val Lys Ile Trp
                165                 170                 175
Phe Gln Asn Arg Arg Ser Lys Phe Lys Lys Leu Tyr Lys Asn Gly Glu
            180                 185                 190
Val Pro Leu Glu His Ser Pro Asn Asn Ser Asp Ser Met Ala Cys Asn
        195                 200                 205
Ser Pro Pro Ser Pro Ala Leu Trp Asp Thr Ser His Ser Thr Pro
    210                 215                 220
Ala Pro Ala Arg Ser Gln Leu Pro Pro Leu Pro Tyr Ser Ala Ser
225                 230                 235                 240
Pro Ser Tyr Leu Asp Asp Pro Thr Asn Ser Trp Tyr His Ala Gln Asn
                245                 250                 255
Leu Ser Gly Pro His Leu Gln Gln Pro Pro Gln Pro Ala Thr Leu
            260                 265                 270
His His Ala Ser Pro Gly Pro Pro Asn Pro Gly Ala Val Tyr
        275                 280                 285

<210> SEQ ID NO 3
<211> LENGTH: 860
<212> TYPE: DNA
<213> ORGANISM: Homo sapiens

<400> SEQUENCE: 3
atgagtggct ccttcgatcg caagctcagc agcatcctca ccgacatctc cagctccctt    60
agctgccatg cgggctccaa ggactcgcct accctgcccg agtcttctgt cactgacctg   120
ggctactaca gcgctcccca gcacgattac tactcgggcc agccctatgg ccagacggtg   180
aaccectaca cctaccacca ccaattcaat ctcaatgggc ttgcaggcac gggcgcttac   240
tcgcccaagt cggaatatac ctacggagcc tcctaccggc aatacggggc gtatcgggag   300
cagccgctgc cagcccagga cccagtgtcg gtgaaggagg agccggaagc agaggtgcgc   360
atggtgaatg ggaagcccaa gaaggtccga agccgcgta caatctactc cagctaccag   420
ctggccgccc tgcagcgccg cttccagaag gcccagtacc tggcgctgcc cgagcgcgcc   480
gagctggccg cgcagctggg cctcacgcag acacaggtga aaatctggtt ccagaaccgc   540
cgttccaagt tcaagaaact ctacaagaac aaggtgccgct ggagcacagt cccaataaca   600
gtgattccat ggcctgcaac tcaccaccat cacccgcccc ctgggacacc tcttcccact   660
ccactccggc ccctgccgc agtcagctgc cccgccgct cccatacagt gcctccccca   720
gctacctgga cgaccccacc aactcctggt atcacgcaca gaacctgagt ggaccccact   780
tacagcagca gccgcctcag ccagccaccc tgcaccatgc ctctcccggg cccccgccca   840
accctggggc tgtgtactga                                                860
```

<210> SEQ ID NO 4
<211> LENGTH: 255
<212> TYPE: PRT
<213> ORGANISM: Homo sapiens

<400> SEQUENCE: 4

```
Met Ser Gly Ser Phe Asp Arg Lys Leu Ser Ser Ile Leu Thr Asp Ile
 1               5                  10                  15

Ser Ser Ser Leu Ser Cys His Ala Gly Ser Lys Asp Ser Pro Thr Leu
            20                  25                  30

Pro Glu Ser Ser Val Thr Asp Leu Gly Tyr Tyr Ser Ala Pro Gln His
        35                  40                  45

Asp Tyr Tyr Ser Gly Gln Pro Tyr Gly Gln Thr Val Asn Pro Tyr Thr
    50                  55                  60

Tyr His His Gln Phe Asn Leu Asn Gly Leu Ala Gly Thr Gly Ala Tyr
65                  70                  75                  80

Ser Pro Lys Ser Glu Tyr Thr Tyr Gly Ala Ser Tyr Arg Gln Tyr Gly
                85                  90                  95

Ala Tyr Arg Glu Gln Pro Leu Pro Ala Gln Asp Pro Val Ser Val Lys
            100                 105                 110

Glu Glu Pro Glu Ala Glu Val Arg Met Val Asn Gly Lys Pro Lys Lys
        115                 120                 125

Val Arg Lys Pro Arg Thr Ile Tyr Ser Ser Tyr Gln Leu Ala Ala Leu
    130                 135                 140

Gln Arg Arg Phe Gln Lys Ala Gln Tyr Leu Ala Leu Pro Glu Arg Ala
145                 150                 155                 160

Glu Leu Ala Ala Gln Leu Gly Leu Thr Gln Thr Gln Val Lys Ile Trp
                165                 170                 175

Phe Gln Asn Arg Arg Ser Lys Phe Lys Lys Leu Tyr Lys Asn Arg Cys
            180                 185                 190

Arg Trp Ser Thr Val Pro Ile Thr Val Ile Pro Trp Pro Ala Thr His
        195                 200                 205

His His His Pro Pro Ser Gly Thr Pro Leu Pro Thr Pro Leu Arg Pro
    210                 215                 220

Leu Pro Ala Val Ser Cys Pro Arg Arg Ser His Thr Val Pro Pro Pro
225                 230                 235                 240

Ala Thr Trp Thr Thr Pro Pro Thr Pro Gly Ile Thr His Arg Thr
                245                 250                 255
```

<210> SEQ ID NO 5
<211> LENGTH: 1906
<212> TYPE: DNA
<213> ORGANISM: Homo sapiens
<220> FEATURE:
<221> NAME/KEY: misc_feature
<222> LOCATION: (0)...(0)
<223> OTHER INFORMATION: N at any position may be an A, T, G, or C

<400> SEQUENCE: 5

```
gtgacgcgcg taatacaatc actatagggc gaattgggta ccgggccccc cctcgaggtc      60
gacggtatcg ataagcttga tatcgaattc ctgcagagct cgaaggaacc acgaggtggc     120
gcgctagcac tgcgttcgcc cggcgaggca nggcgagtgg acgtgggtc nacgagcga      180 gccgggcagg ctgggaactg anatttggat tctctccccc aaanaaaggc gaagggcnaa     240
atggggtgtg ggaggcaggg atnagctana cgttgggaac agctancatg acctangggg     300
cccagcttgg tgggctagac nggactaaaa tctgggggtc cccacagagg gganccattc     360
```

```
ttcanggntn nncngqtgct rcgaggantt cagtggagcn gtacanctcc cnsctactgg      420
agatgargaa ngtnctaagc ggtctanaca cntctgccta caaccacatg ttcacacgcg      480
gatggccctc cactcatnct gcctgcaccc cgcccccgac acactcctgc ntgcatgtac      540
ctctgttgga tnctgtggaa cacatnaaan tcctcacatc acncacccca aatananttc      600
ktcccatgca nccagtcccc aanaagtntc ccaattccnc antgctgtcc cntnataccn      660
caaaatctgc ccttcarant tactnnnaak cacacagtca caganccagc ctgtgtccac      720
ccaacctcgt ggggacccaa gtccttgcta ccttcagcaa gaatggggnc atctgtgaaa      780
ctgcacatac atanctttgg gagataattc tggtatcacc ggacaggctg tacatcccca      840
acaacctcta aatccacaca ggtctgcttc cccttctcca ataggatcct cctagtgcta      900
aattatgtct ttcataggct caagaacatt ncttngcccg gtgggcacct tcctaaataa      960
aaagaaaatt ttttaaatta cgttttgta attatgtaat acaaggatat aatagcaatg     1020
actgcattgc tattaagata atatattaat atcatatatt caaacattct ctttcaccta     1080
aaaggtgttt tccttttctt ctgattttaa ganaaaccat tttcaggggc tgtgagtcct     1140
caccactttg ggtacatttg tgtgcctgtc atttgcacag tgcgtgcaca cgtgtgcaca     1200
cacacacaac catacccccac cttagaccat ctctttccac aaacacacaa tgggcaaact     1260
cccctccttg cccacctcac ctaagcccat ctctcatccc ccagccagag aaacagactg     1320
acagatcctg ggggctccac agancaaccc ttcccctcca cctccacgcc cctccttcag     1380
aaaacttatc tgggctggag ctacaagaan nansnngggt gtgtgtgtgt gtgtgtgtgt     1440
gtgtgtgtgt gtgtgtgtgt gtgttttgag taacaacaaa gactggggaa aagaagaga     1500 gaggagggag gagagaagga aaaggggag agagagagag agagaggaga gcataggagc     1560
gagagagcaa aagcgtgttt tgcctggaag gcaagacttg cagccaatca gcgcgtanga     1620
gcctccctcg gcgactccac tattgagtct ataaccggct ggccgggcgg agctggcanc     1680
atttgattgt ggcttgggac gcgaggagag gcgcgcagcg accgcctgac ggcaggcaat     1740
ggtgtnngcg cctctcggcc tccccctccc ccagacgcg gccgggtcct cccttcgcct     1800
tctggacaca caccccctgcc tcgtctcttc cgcctctctt gcactccggt ccgttcctgt     1860
cctctgcgga ggccagccct ggggaggtgc agcgcccgcc aggatg                    1906
```

<210> SEQ ID NO 6
<211> LENGTH: 20
<212> TYPE: DNA
<213> ORGANISM: Homo sapiens

<400> SEQUENCE: 6

```
gctcacggac ccatacgagt                                                   20
```

<210> SEQ ID NO 7
<211> LENGTH: 21
<212> TYPE: DNA
<213> ORGANISM: Homo sapiens

<400> SEQUENCE: 7

```
caaggaaaaa tcgctgggtg g                                                 21
```

<210> SEQ ID NO 8
<211> LENGTH: 19
<212> TYPE: DNA
<213> ORGANISM: Homo sapiens

<400> SEQUENCE: 8

```
gccacagcac caatccatc                                                  19

<210> SEQ ID NO 9
<211> LENGTH: 19
<212> TYPE: DNA
<213> ORGANISM: Homo sapiens

<400> SEQUENCE: 9
gctagacagg gagacatgg                                                  19

<210> SEQ ID NO 10
<211> LENGTH: 19
<212> TYPE: DNA
<213> ORGANISM: Homo sapiens

<400> SEQUENCE: 10
cccatctgga gctggtttc                                                  19

<210> SEQ ID NO 11
<211> LENGTH: 19
<212> TYPE: DNA
<213> ORGANISM: Homo sapiens

<400> SEQUENCE: 11
cttatctggg ctggagcta                                                  19

<210> SEQ ID NO 12
<211> LENGTH: 19
<212> TYPE: DNA
<213> ORGANISM: Homo sapiens

<400> SEQUENCE: 12
gcgctgattg gctgcaagt                                                  19

<210> SEQ ID NO 13
<211> LENGTH: 19
<212> TYPE: DNA
<213> ORGANISM: Homo sapiens

<400> SEQUENCE: 13
ctcccataca cctcacccg                                                  19

<210> SEQ ID NO 14
<211> LENGTH: 1413
<212> TYPE: DNA
<213> ORGANISM: Homo sapiens

<400> SEQUENCE: 14
tcttgcactc cggtccgttc ctgtcctctg cggaggccag ccctggggag gtgcagcgcc      60
cgccaggatg agtggctcct tcgatcgcaa gctcagcagc atcctcaccg acatctccag     120
ctcccttagc tgccatgcgg gctccaagga ctcgcctacc ctgcccgagt cttctgtcac     180
tgacctgggc tactacagcg ctccccagca cgattactac tcgggccagc ctatggcca     240 gacggtgaac cctacacct accaccacca attcaatctc aatgggcttg caggcacggg     300
cgcttactcg cccaagtcgg aatataccta cggagcctcc taccgcaat acggggcgta     360 tcgggagcag ccgctgccag cccaggaccc aggtgagggc cacggggtcg cgaggacagt     420
gggagacact ggaagagtcg gtgggcggaa gcgaggggcg tccggcgggg ccctggaggg     480
tcgcaggagt cgcaggccga ggctgaaccg cccctcttcc gcccggtgcg ttccccgcag     540
```

-continued

```
tgtcggtgaa ggaggagccg gaagcagagg tgcgcatggt gaatgggaag cccaagaagg       600
tccgaaagcc gcgtacaatc tactccagct accagctggc cgccctgcag cgccgcttcc       660
agaaggccca gtacctggcg ctgcccgagc gcgccgagct ggccgcgcag ctgggcctca       720
cgcagacaca ggttggtgtt tggctgtcca gggtcgcggg ggcgcgcggg accccgtagt       780
tccccgcgcg ctgccgagtc tggctggcca ctgaagggcc ctgcgggctc ctggaactct       840
tgcctttggg acgcacaatt ctatcccaga tccaagaaaa ctgggagtca ggaagcctgt       900
tttttgcctg attcttatgt gaaattgggt tctggccttt cttttttcttg ctaggttct       960 tgccagggtt gtttagcatt ctgagaggct aactagctac ccctttcttc tctggcccag      1020
gtgaaaatct ggttccagaa ccgccgttcc aagttcaaga aactctacaa gaacggggag      1080
gtgccgctgg agcacagtcc caataacagt gattccatgg cctgcaactc accaccatca      1140
cccgccctct gggacacctc ttcccactcc actccggccc ctgccgcag tcagctgccc       1200 ccgccgctcc catacagtgc ctcccccagc tacctggacg accccaccaa ctcctggtat      1260
cacgcacaga acctgagtgg accccactta cagcagcagc cgcctcagcc agccaccctg      1320
caccatgcct ctcccgggcc cccgcccaac cctggggctg tgtactgagc accatctggc      1380 ctgcacccctt gacaaaggac cccaggacca ggc                                 1413
```

<210> SEQ ID NO 15
<211> LENGTH: 100
<212> TYPE: PRT
<213> ORGANISM: Mus musculus

<400> SEQUENCE: 15

```
Ser Val Lys Glu Glu Pro Glu Ala Glu Val Arg Met Val Asn Gly Lys
  1               5                  10                  15

Pro Lys Lys Val Arg Lys Pro Arg Thr Ile Tyr Ser Ser Tyr Gln Leu
                 20                  25                  30

Ala Ala Leu Gln Arg Arg Phe Gln Lys Ala Gln Tyr Leu Ala Leu Pro
             35                  40                  45

Glu Arg Ala Glu Leu Ala Ala Gln Leu Gly Leu Thr Gln Thr Gln Val
         50                  55                  60

Lys Ile Trp Phe Gln Asn Arg Arg Ser Lys Phe Lys Lys Leu Tyr Lys
 65                  70                  75                  80

Asn Gly Glu Val Pro Leu Glu His Ser Pro Asn Asn Ser Asp Ser Met
                 85                  90                  95

Ala Cys Asn Ser
            100
```

<210> SEQ ID NO 16
<211> LENGTH: 101
<212> TYPE: PRT
<213> ORGANISM: Axolotl

<400> SEQUENCE: 16

```
Ser Val Lys Glu Glu Pro Glu Pro Glu Val Arg Met Val Asn Gly Lys
  1               5                  10                  15

Pro Lys Lys Ile Arg Lys Pro Arg Thr Ile Tyr Ser Ser Tyr Gln Leu
                 20                  25                  30

Ala Ala Leu Gln Arg Arg Phe Gln Lys Ala Gln Tyr Leu Ala Leu Pro
             35                  40                  45

Glu Arg Ala Glu Leu Ala Ala Gln Leu Gly Leu Thr Gln Thr Gln Val
         50                  55                  60
```

```
Lys Ile Trp Phe Gln Asn Arg Arg Ser Lys Phe Lys Lys Leu Tyr Lys
 65                  70                  75                  80

Asn Gly Glu Val Pro Gly Met Glu His Ser Pro Asp Asn Ser Asp Ser
                 85                  90                  95

Met Ala Cys Asn Ser
            100

<210> SEQ ID NO 17
<211> LENGTH: 101
<212> TYPE: PRT
<213> ORGANISM: Newt

<400> SEQUENCE: 17

Thr Val Lys Glu Glu Pro Glu Pro Glu Val Arg Met Val Asn Gly Lys
 1               5                  10                  15

Pro Lys Lys Ile Arg Lys Pro Arg Thr Ile Tyr Ser Ser Tyr Gln Leu
                20                  25                  30

Ala Ala Leu Gln Arg Arg Phe Gln Lys Ala Gln Tyr Leu Ala Leu Pro
            35                  40                  45

Glu Arg Ala Glu Leu Ala Ala Gln Leu Gly Leu Thr Gln Thr Gln Val
     50                  55                  60

Lys Ile Trp Phe Gln Asn Arg Arg Ser Lys Phe Lys Lys Leu Tyr Lys
 65                  70                  75                  80

Asn Gly Glu Val Pro Gly Met Glu His Ser Pro Asn Asn Ser Asp Ser
                 85                  90                  95

Met Ala Cys Asn Ser
            100

<210> SEQ ID NO 18
<211> LENGTH: 100
<212> TYPE: PRT
<213> ORGANISM: Zebrafish

<400> SEQUENCE: 18

Ala Val Lys Glu Glu Pro Glu Thr Glu Val Arg Met Val Asn Gly Lys
 1               5                  10                  15

Pro Lys Lys Ile Arg Lys Pro Arg Thr Ile Tyr Ser Ser Tyr Gln Leu
                20                  25                  30

Ala Ala Leu Gln Arg Arg Phe Gln Lys Ala Gln Tyr Leu Ala Leu Pro
            35                  40                  45

Glu Arg Ala Glu Leu Ala Ala Gln Leu Gly Leu Thr Gln Thr Gln Val
     50                  55                  60

Lys Ile Trp Phe Gln Asn Arg Arg Ser Lys Phe Lys Lys Leu Tyr Lys
 65                  70                  75                  80

Asn Gly Glu Val Pro Leu Glu His Ser Pro Ala Asn Ser Asp Ser Met
                 85                  90                  95

Ala Cys Asn Ser
        100

<210> SEQ ID NO 19
<211> LENGTH: 101
<212> TYPE: PRT
<213> ORGANISM: Xenopus

<400> SEQUENCE: 19

Ser Val Lys Glu Glu Pro Glu Thr Glu Val Arg Met Val Asn Gly Lys
 1               5                  10                  15

Pro Lys Lys Ile Arg Lys Pro Arg Thr Ile Tyr Ser Ser Tyr Gln Leu
```

```
                    20                  25                  30

Ala Ala Leu Gln Arg Arg Phe Gln Lys Ala Gln Tyr Leu Ala Leu Pro
            35                  40                  45

Glu Arg Ala Glu Leu Ala Ala Gln Leu Gly Leu Thr Gln Thr Gln Val
    50                  55                  60

Lys Ile Trp Phe Gln Asn Arg Arg Ser Lys Phe Lys Lys Leu Tyr Lys
65                  70                  75                  80

Asn Gly Glu Gly Pro Asp Met Glu His Ser Pro Asn Asn Ser Asp Ser
                85                  90                  95

Met Ala Gly Asn Ser
            100

<210> SEQ ID NO 20
<211> LENGTH: 100
<212> TYPE: PRT
<213> ORGANISM: Homo sapiens

<400> SEQUENCE: 20

Glu Lys Glu Asp Leu Glu Pro Glu Ile Arg Ile Val Asn Gly Lys Pro
1               5                   10                  15

Lys Lys Val Arg Lys Pro Arg Thr Ile Tyr Ser Ser Phe Gln Leu Ala
            20                  25                  30

Ala Leu Gln Arg Arg Phe Gln Lys Thr Gln Tyr Leu Ala Leu Pro Glu
            35                  40                  45

Arg Ala Glu Leu Ala Ala Gln Leu Gly Leu Thr Gln Thr Gln Val Lys
    50                  55                  60

Ile Trp Phe Gln Asn Arg Arg Ser Lys Phe Lys Lys Met Trp Lys Ser
65                  70                  75                  80

Gly Glu Ile Pro Ser Glu Gln His Pro Gly Ala Ser Ala Ser Pro Pro
                85                  90                  95

Cys Ala Ser Pro
            100

<210> SEQ ID NO 21
<211> LENGTH: 66
<212> TYPE: PRT
<213> ORGANISM: Homo sapiens

<400> SEQUENCE: 21

Val Arg Lys Pro Arg Thr Ile Tyr Ser Ser Phe Gln Leu Ala Ala Leu
1               5                   10                  15

Gln Arg Arg Phe Gln Lys Thr Gln Tyr Leu Ala Leu Pro Glu Arg Ala
            20                  25                  30

Glu Leu Ala Ala Ser Leu Gly Leu Thr Gln Thr Gln Val Lys Ile Trp
            35                  40                  45

Phe Gln Asn Lys Arg Ser Lys Ile Lys Lys Ile Met Lys Asn Gly Glu
    50                  55                  60

Asn Pro
65

<210> SEQ ID NO 22
<211> LENGTH: 66
<212> TYPE: PRT
<213> ORGANISM: Homo sapiens

<400> SEQUENCE: 22

Ile Arg Lys Pro Arg Thr Ile Tyr Ser Ser Leu Gln Leu Gln Ala Leu
1               5                   10                  15
```

-continued

```
Asn Arg Arg Phe Gln Gln Thr Gln Tyr Leu Ala Leu Pro Glu Arg Ala
            20                  25                  30
Glu Leu Ala Ala Ser Leu Gly Leu Thr Gln Thr Gln Val Lys Ile Trp
        35                  40                  45
Phe Gln Asn Lys Arg Ser Lys Phe Lys Lys Leu Met Lys Gln Gly Gly
    50                  55                  60
Ala Ala
65

<210> SEQ ID NO 23
<211> LENGTH: 66
<212> TYPE: PRT
<213> ORGANISM: Homo sapiens

<400> SEQUENCE: 23

Ile Arg Lys Pro Arg Thr Ile Tyr Ser Ser Leu Gln Leu Gln Ala Leu
 1               5                  10                  15
Asn His Arg Phe Gln Gln Thr Gln Tyr Leu Ala Leu Pro Glu Arg Ala
            20                  25                  30
Glu Leu Ala Ala Ser Leu Gly Leu Thr Gln Thr Gln Val Lys Ile Trp
        35                  40                  45
Phe Gln Asn Lys Arg Ser Lys Phe Lys Lys Leu Leu Lys Gln Gly Ser
    50                  55                  60
Asn Pro
65

<210> SEQ ID NO 24
<211> LENGTH: 99
<212> TYPE: PRT
<213> ORGANISM: Homo sapiens

<400> SEQUENCE: 24

Pro Arg Leu Ser Pro Glu Pro Ser Glu Arg Arg Pro Gln Ala Ala Ala
 1               5                  10                  15
Lys Lys Leu Arg Lys Pro Arg Thr Ile Tyr Ser Ser Leu Gln Leu Gln
            20                  25                  30
His Leu Asn Gln Arg Phe Gln His Thr Gln Tyr Leu Ala Leu Pro Glu
        35                  40                  45
Arg Ala Gln Leu Ala Ala Gln Leu Gly Leu Thr Gln Thr Gln Val Lys
    50                  55                  60
Ile Trp Phe Gln Asn Lys Arg Ser Lys Tyr Lys Lys Leu Leu Lys Gln
65                  70                  75                  80
Asn Ser Gly Gly Gln Glu Gly Asp Phe Pro Gly Arg Thr Phe Ser Val
                85                  90                  95
Ser Pro Cys

<210> SEQ ID NO 25
<211> LENGTH: 13
<212> TYPE: DNA
<213> ORGANISM: Artificial Sequence
<220> FEATURE:
<221> NAME/KEY: misc_feature
<222> LOCATION: (0)...(0)
<223> OTHER INFORMATION: r at any position = g or a

<400> SEQUENCE: 25
gccgccrcca ugg                                                              13
```